United States Patent
Miesel et al.

(10) Patent No.: US 8,688,221 B2
(45) Date of Patent: *Apr. 1, 2014

(54) COLLECTING POSTURE AND ACTIVITY INFORMATION TO EVALUATE THERAPY

(75) Inventors: Keith A. Miesel, St. Paul, MN (US); Kenneth T. Heruth, Edina, MN (US); Gregory F. Molnar, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 11 days.

This patent is subject to a terminal disclaimer.

(21) Appl. No.: 13/401,348

(22) Filed: Feb. 21, 2012

(65) Prior Publication Data
US 2012/0150258 A1 Jun. 14, 2012

Related U.S. Application Data

(63) Continuation of application No. 11/691,381, filed on Mar. 26, 2007, now Pat. No. 8,135,473, which is a continuation-in-part of application No. 11/106,051, filed on Apr. 14, 2005, now Pat. No. 7,313,440.

(60) Provisional application No. 60/562,024, filed on Apr. 14, 2004, provisional application No. 60/785,677, filed on Mar. 24, 2006.

(51) Int. Cl.
*A61N 1/36* (2006.01)

(52) U.S. Cl.
USPC ........ 607/45; 607/2; 607/27; 607/46; 607/48; 607/62

(58) Field of Classification Search
None
See application file for complete search history.

(56) References Cited

U.S. PATENT DOCUMENTS

| 4,297,685 A | 10/1981 | Brainard, II |
| 4,550,736 A | 11/1985 | Broughton et al. |
| 4,771,780 A | 9/1988 | Sholder |

(Continued)

FOREIGN PATENT DOCUMENTS

| DE | 198 31 109 | 1/2000 |
| DE | 100 24 103 | 11/2001 |

(Continued)

OTHER PUBLICATIONS

Request for Continued Examination and Responsive Amendment dated May 29, 2012 for U.S. Appl No. 11/691,425, (13 pgs.).

(Continued)

*Primary Examiner* — Kennedy Schaetzle
(74) *Attorney, Agent, or Firm* — Shumaker & Sieffert, P.A.

(57) ABSTRACT

A medical device, programmer, or other computing device may determine values of one or more activity and, in some embodiments, posture metrics for each therapy parameter set used by the medical device to deliver therapy. The metric values for a parameter set are determined based on signals generated by the sensors when that therapy parameter set was in use. Activity metric values may be associated with a postural category in addition to a therapy parameter set, and may indicate the duration and intensity of activity within one or more postural categories resulting from delivery of therapy according to a therapy parameter set. A posture metric for a therapy parameter set may indicate the fraction of time spent by the patient in various postures when the medical device used a therapy parameter set. The metric values may be used to evaluate the efficacy of the therapy parameter sets.

21 Claims, 15 Drawing Sheets

(56) References Cited

U.S. PATENT DOCUMENTS

| | | |
|---|---|---|
| 4,776,345 A | 10/1988 | Cohen et al. |
| 4,846,195 A | 7/1989 | Alt |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,732,696 A | 3/1998 | Rapoport et al. |
| 5,782,884 A | 7/1998 | Stotts et al. |
| 5,851,193 A | 12/1998 | Arikka et al. |
| 5,895,371 A | 4/1999 | Levitas et al. |
| 5,904,708 A | 5/1999 | Goedeke |
| 5,919,149 A | 7/1999 | Allum |
| 5,941,906 A | 8/1999 | Barreras, Sr. et al. |
| 5,944,680 A | 8/1999 | Christopherson et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,433,690 B2 | 8/2002 | Petelenz et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Cho et al. |
| 6,735,474 B1 | 5/2004 | Loeb et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 | 11/2005 | Cho et al. |
| 6,997,882 B1 | 2/2006 | Parker et al. |
| 7,130,689 B1 | 10/2006 | Turcott |
| 7,162,304 B1 | 1/2007 | Bradley |
| 7,209,787 B2 | 4/2007 | DiLorenzo |
| 7,313,440 B2 * | 12/2007 | Miesel .............. 607/19 |
| 7,369,896 B2 | 5/2008 | Gesotti |
| 8,135,473 B2 * | 3/2012 | Miesel et al. ........... 607/49 |
| 8,308,661 B2 * | 11/2012 | Miesel et al. ......... 600/587 |
| 2001/0037067 A1 | 11/2001 | Tchou et al. |
| 2001/0049471 A1 | 12/2001 | Suzuki et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1 | 6/2004 | Ni et al. |
| 2004/0199217 A1 | 10/2004 | Lee et al. |
| 2005/0021103 A1 | 1/2005 | DiLorenzo |
| 2005/0021104 A1 | 1/2005 | DiLorenzo |
| 2005/0042589 A1 | 2/2005 | Hatlestad et al. |
| 2005/0060001 A1 | 3/2005 | Singhal et al. |
| 2005/0113710 A1 | 5/2005 | Stahmann et al. |
| 2005/0119703 A1 | 6/2005 | DiLorenzo |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | DiLorenzo |
| 2006/0293720 A1 | 12/2006 | DiLorenzo |
| 2007/0046408 A1 | 3/2007 | Shim |
| 2007/0073355 A1 | 3/2007 | DiLorenzo |
| 2007/0142862 A1 | 6/2007 | DiLorenzo |

FOREIGN PATENT DOCUMENTS

| | | |
|---|---|---|
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 A | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |

(56) References Cited

FOREIGN PATENT DOCUMENTS

| | | |
|---|---|---|
| WO | WO 2005/028029 | 3/2005 |
| WO | WO 2005/035050 | 4/2005 |

OTHER PUBLICATIONS

Office Action dated Mar. 27, 2012 for U.S. Appl. No. 13/362,785, (10 pgs.).
Responsive Amendment dated Jun. 27, 2012 for U.S. Appl. No. 13/362,785, (13 pgs.).
Final Office Action dated Feb. 27, 2012 for U.S. Appl. No. 11/691,425, (16 pgs.).
Responsive Amendment dated Apr. 27, 2012 for U.S. Appl. No. 11/691,425, (10 pgs.).
Advisory Action dated May 3, 2012 for U.S. Appl. No. 11/691,425, (3 pgs.).
Office Action dated Jul. 26, 2012 for U.S. Appl. No. 13/362,785, (5 pgs.).
Amzica, "Physiology of Sleep and Wakefulness as it Relates to the Physiology of Epilepsy," Journal of Clinical Neurophysiology, American Clinical Neurophysiology Society, 19(6), pp. 488-503, (2002).
Dinner, "Effect of Sleep on Epilepsy," Journal of Clinical Neurophysiology, American Clinical Neurophysiology Society, 19(6), pp. 504-513, (2002).
Mendez et al. "Interactions Between Sleep and Epilepsy," Journal of Clinical Neurophysiology, American Clinical Neurophysiology Society, 18(2), pp. 106-127, (2001).
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).
"MiniMitter® Physiological and Behavioral Monitoring for Humans and Animals," http://www.minimitter.com/Products/Actiwatch, 3 pgs. Feb. 20, 2006.
"IBM & Citzen Watch develop Linux-based 'WatchPad'," 5 pgs., http://www.linuxdevices.com/news/NS6580187845.html, Feb. 20, 2006.
"Design Competition: Runners-Up for the Best Three Designs," EPN, vol. 26, No. 1, 1 pg., (2002).
"Watch," Wikipedia, the free encyclopedia, 6 pgs., http://en.wikipedia.org/wiki/Watch, Feb. 20, 2006.
Kassam, "2005 EDP Topic 'MK4': Tremor Data-Logger for Parkinson's Disease Patients," http://www.ee.ryerson.ca/~courses/edp2005/MK4.html, 3 pgs., Feb. 20, 2006.
Tuisku, "Motor Activity Measured by Actometry in Neuropsychiatric Disorders," Department of Psychiatry, University of Helsinki, Helsinki, Finland, 115 pgs. (2002).
Smith et al., "Presleep Cognitions in Patients with Insomnia Secondary to Chronic Pain," Journal of Behavioral Medicine, vol. 24, No. 1, pp. 93-114, (2001).
Smith et al. "How do sleep disturbance and chronic pain inter-relate? Insights from the longitudinal and cognitive-behavioral clinical trials literature," Sleep Medicine Reviews, YSMRV 286, pp. 1-14, (2003).
Goodrich et al., "The Prediction of Pain Using Measures of Sleep Quality," Pain Digest, 8:23-25, (1998).
"Analysis of heart rate dynamics by methods derived from nonlinear mathematics: Clinical applicability and prognostic significance" http:/herkules.oulu.fi.isbn9514250133/html, 4 pgs., (2004).
Kerr et al., "Analysis of the sit-stand-sit movement cycle in normal subjects," Clinical Biomechanics, vol. 12, No. 4, pp. 236-245, (1997).
Aminian et al. "Physical Activity Monitoring Based on Accelerometry: Validation and Comparison with Video Observation," Medical & Biological Engineering & Computing, vol. 37, No. 2, pp. 304-308 (1999).
Medcare—A Global Leader in Sleep Diagnostics, Embletta Recording System, http://www.medcare.com/products/diagnostic/embletta/, 2 pgs. Jan. 31, 2005.
Medcare—A Global Leader in Sleep Diagnostics, Somnologica for Embletta, http://www.medcare.com/products/diagnostic/embletta/SomnoEmbletta/index.asp, 1 pg. Jan. 31, 2005.
MAP Medizin-Technologie GmbH, Poly-MESAM®, http://195.244.124.130/map/de/eng/map_med.nsf/smsall/70564A3FCBE41188AC1256EF4 . . . , 4 pgs. Jan. 31, 2005.
Merlin, http://www.aha.ru/~pir/english/merlin/, 4 pgs. Jan. 31, 2005.
Sleep Solutions—PR Newswire: Sleep Solutions Introduces NovaSom™ QSG™ for PSG . . . , http://www.steep-solutions.com/press_room/novasom.htm, 2 pgs. Jan. 31, 2005.
Itamar Medical Information, http://itamar-medical.com/content.asp?id-id=31, 2 pgs. Jan. 31, 2005.
Criticare System Inc.,—504DX Portable Pulse Oximeter, http://www.csiusa.com/504dx.html, 4 pgs. Jan. 31, 2005.
Snap® Laboratories, Product Fact Sheet, http://www.snaplab.com/mp_fact.htm, 2 pgs., Jan. 31, 2005.
Sleep Strip & Bite Strip, http://ww.quietsleep.com/snoringapnea/sleepstrip.htm, 8 pgs. Jan. 31, 2005.
"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.
"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.
"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.
van Dam et al., "Measuring physical activity in patients after surgery for a malignant tumour in the leg," The Journal of Bone & Joint Surgery, vol. 83-B, No. 7, pp. 1015-1019 (Sep. 2001).
Office Action dated Apr. 23, 2008 for U.S. Appl. No. 11/796,811 (6 pgs.).
Office Action dated May 6, 2008 for U.S. Appl. No. 10/825,955 (13 pgs.).
Office Action dated May 9, 2008 for U.S. Appl. No. 11/081,857 (10 pgs.).
Response dated Jul. 2, 2008 for U.S. Appl. No. 10/825,955 (13 pgs.).
Responsive Amendment dated Aug. 7, 2008 for U.S. Appl. No. 11/081,857 (13 pgs.).
Responsive Amendment dated Aug. 22, 2008 for U.S. Appl. No. 11/796,811 (13 pgs.).
Responsive Amendment dated Feb. 19, 2009 for U.S. Appl. No. 11/796,811 (15 pgs.).
Office Action dated Aug. 4, 2009 for U.S. Appl. No. 11/413,619 (9 pgs.).
Response dated Nov. 4, 2009 for U.S. Appl. No. 11/413,619 (7 pgs.).
Office Action dated Feb. 25, 2008 for U.S. Appl. No. 11/081,872 (5 pgs.).
Response to Office Action dated May 27, 2008 for U.S. Appl. No. 11/081,872 (2 pgs.).
Office Action dated Nov. 19, 2008 for U.S. Appl. No. 11/796,811 (7 pgs.).
Office Action dated Mar. 11, 2009 for U.S. Appl. No. 10/826,926 (25 pgs.).
Responsive Amendment dated Aug. 11, 2009 for U.S. Appl. No. 10/826,925 (12 pgs.).
Office Action dated May 8, 2009 for U.S. Appl. No. 11/691,391 (8 pgs.).
Responsive Amendment dated Aug. 5, 2009 for U.S. Appl. No. 11/691,391 (10 pgs.).
Office Action dated May 29, 2009 for U.S. Appl. No. 11/081,811 (13 pgs.).
Responsive Amendment dated Aug. 31, 2009 for U.S. Appl. No. 11/081,811 (17 pgs.).
Office Action dated Dec. 31, 2009 for U.S. Appl. No. 11/691,391 (6 pgs.).
Office Action dated Jan. 12, 2010 for U.S. Appl. No. 11/691,411 (8 pgs.).
Office Action dated Mar. 12, 2010 for U.S. Appl. No. 11/691,413 (7 pgs.).

(56) References Cited

OTHER PUBLICATIONS

Responsive Amendment dated Apr. 12, 2010 for U.S. Appl. No. 11/691,411 (12 pgs.).
Office Action dated May 19, 2010 for U.S. Appl. No. 11/691,405 (12 pgs.).
Office Action dated May 20, 2010 for U.S. Appl. No. 12/248,622 (6 pgs.).
Responsive Amendment dated Jun. 9, 2010 for U.S. Appl. No. 11/691,413 (16 pgs.).
Response dated Mar. 31, 2010 for U.S. Appl. No. 11/691,391 (5 pgs.).
Office Action dated Apr. 22, 2010 for U.S. Appl. No. 11/691,423 (8 pgs.).
Office Action dated May 6, 2010 for U.S. Appl. No. 12/017,918 (11 pgs.).
Office Action dated Jul. 14, 2010 for U.S. Appl. No. 11/691,413 (7 pgs.).
Responsive Amendment dated Jul. 22, 2010 for U.S. Appl. No. 11/691,423 (15 pgs.).
Office Action dated Aug. 2, 2010 for U.S. Appl. No. 12/351,414 (21 pgs.).
Office Action dated Aug. 5, 2010 for U.S. Appl. No. 12/248,609 (8 pgs.).
Responsive Amendment dated Aug. 5, 2010 for U.S. Appl. No. 12/017,918 (16 pgs.).
Responsive Amendment dated Aug. 5, 2010 for U.S. Appl. No. 12/248,622 (10 pgs.).
Response dated Sep. 14, 2010 for U.S. Appl. No. 11/691,413 (7 pgs.).
Response dated Oct. 1, 2010 for U.S. Appl. No. 12/351,414 (10 pgs.).
Advisory Action dated Oct. 12, 2010 for U.S. Appl. No. 12/351,414 (3 pgs.).
Response dated Nov. 4, 2010 for U.S. Appl. No. 12/248,609 (10 pgs.).
Office Action dated Sep. 29, 2010 for U.S. Appl. No. 12/248,622, (7 pgs.).
Response dated Nov. 18, 2010 for U.S. Appl. No. 12/248,622 (10 pgs.).
Office Action dated Dec. 14, 2010 for U.S. Appl. No. 11/691,413, (6 pgs.).
Office Action dated Dec. 22, 2010 for U.S. Appl. No. 12/248,609 (7 pgs.).
Office Action dated Dec. 23, 2010 for U.S. Appl. No. 12/856,255 (5 pgs.).
Advisory Action dated Feb. 28, 2011 for U.S. Appl. No. 12/248,609 (3 pgs.).
Response dated Mar. 14, 2011 for U.S. Appl. No. 11/691,413 (2 pgs.).
Notice of Appeal and Pre-Appeal Brief Request for Review dated Mar. 22, 2011 for U.S. Appl. No. 12/248,609 (6 pgs.).
Responsive Amendment dated Mar. 23, 2011 for U.S. Appl. No. 12/856,255, (9 pgs.).
Office Action dated May 10, 2011 for U.S. Appl. No. 12/248,622 (6 pgs.).
Responsive Amendment dated Aug. 10, 2011 for U.S. Appl. No. 12/248,622 (10 pgs.).
Office Action dated May 10, 2011 for U.S. Appl. No. 12/248,609 (7 pgs.).
Office Action dated Jun. 2, 2011 for U.S. Appl. No. 12/586,255 (7 pgs.).
Responsive Amendment dated Aug. 10, 2011 for U.S. Appl. No. 12/248,609 (11 pgs.).
Responsive Amendment dated Sep. 2, 2011 for U.S. Appl. No. 12/586,255 (9 pgs.).
Final Office Action dated Oct. 20, 2011 for U.S. Appl. No. 12/248,622 (8 pgs.).
Response dated Dec. 20, 2011 for U.S. Appl. No. 12/248,622 (5 pgs.).
Final Office Action dated Oct. 20, 2011 for U.S. Appl. No. 12/248,609 (8 pgs.).
Response dated Dec. 20, 2011 for U.S. Appl. No. 12/248,609 (7 pgs.).
Final Office Action dated Oct. 26, 2011 for U.S. Appl. No. 12/856,255, (8 pgs.).
Request for Continued Examination and Responsive Amendment dated Dec. 15, 2011 for U.S. Appl. No. 12/856,255, (11 pgs.).
Office Action dated Nov. 8, 2011 for U.S. Appl. No. 11/691,425, (12 pgs.).
Final Office Action dated Oct. 20, 2011 for U.S. Appl. No. 12/248,622, (8 pgs.).
Response dated Dec. 20, 2011 for U.S. Appl. No. 12/248,622, (5 pgs.).
Final Office Action dated Oct. 20, 2011 for U.S. Appl. No. 12/248,609, (8 pgs.).
Response dated Dec. 20, 2011 for U.S. Appl. No. 12/248,609, (7 pgs.).
Office Action dated Oct. 14, 2009 for U.S. Appl. No. 11/081,857 (14 pgs.).
Response dated Dec. 14, 2009 for U.S. Appl. No. 11/081,857 (8 pgs.).
Advisory Action dated Jan. 12, 2010 for U.S. Appl. No. 11/081,857 (3 pgs.).
Office Action dated Nov. 6, 2008 for U.S. Appl. No. 11/081,857 (8 pgs.).
Response dated Jan. 6, 2009 for U.S. Appl. No. 11/081,857 (6 pgs).
Decision on Appeal dated Mar. 14, 2012 for U.S. Appl. No. 11/081,857, (7 pgs.).

* cited by examiner

| PARAMETER SET | PARAMETERS | POSTURE | % OF TIME ACTIVE | COUNTS/HOUR |
|---|---|---|---|---|
| 1 | PA = 5.5V<br>PW = 210ms<br>PR = 90Hz | UPRIGHT (52%)<br>RECUMBENT (48%) | 75% (15% HIGH)<br>10% (2% HIGH) | 100<br>10 |
| 2 | PA = 5V<br>PW = 190ms<br>PR = 95Hz | UPRIGHT (45%)<br>RECUMBENT (55%) | 68% (4% HIGH)<br>10% (1% HIGH) | 67<br>12 |
| ••• | | | | |
| N | PA = 4.6V<br>PW = 215ms<br>PR = 80Hz | UPRIGHT (40%)<br>RECUMBENT (60%) | 62% (4% HIGH)<br>8% (1% HIGH) | 72<br>13 |

COLLECTING POSTURE AND ACTIVITY INFORMATION TO EVALUATE THERAPY

This application is a continuation of U.S. application Ser. No. 11/691,381, filed Mar. 26, 2007, which is a continuation-in-part of U.S. application Ser. No. 11/106,051, filed Apr. 14, 2005, which claimed the benefit of U.S. provisional application No. 60/562,024, filed Apr. 14, 2004. U.S. application Ser. no. 11/691,381 also claims the benefit of U.S. provisional application no. 60/785,677, filed Mar. 24, 2006. The entire content of each of these applications is incorporated herein by reference.

TECHNICAL FIELD

The invention relates to medical devices and, more particularly, to medical devices that deliver therapy.

BACKGROUND

In some cases, an ailment may affect a patient's activity level or range of activities by preventing the patient from being active. For example, chronic pain may cause a patient to avoid particular physical activities, or physical activity in general, where such activities increase the pain experienced by the patient. Other ailments that may affect patient activity include movement disorders, such as tremor, Parkinson's disease, multiple sclerosis, epilepsy, or spasticity, which may result in irregular movement or activity, as well as a generally decreased level of activity. The difficulty walking or otherwise moving experienced by patients with movement disorders may cause such patients to avoid movement to the extent possible. Further, depression, mania, bipolar disorder, obsessive-compulsive disorder, or other psychological disorders, and congestive heart failure, cardiac arrhythmia, gastrointestinal disorders, and incontinence are other examples of disorders that may generally cause a patient to be less active. When a patient is inactive, he may be more likely to be recumbent, i.e., lying down, or sitting, and may change postures less frequently. Any of a variety of neurological disorders, including movement disorders, psychological disorders and chronic pain, may negatively patient activity and/or posture.

In some cases, these ailments are treated via a medical device, such as an implantable medical device (IMD). For example, patients may receive an implantable neurostimulator or drug delivery device to treat chronic pain, a movement disorder, or a psychological disorder. Congestive heart failure may be treated by, for example, a cardiac pacemaker or a drug delivery device.

SUMMARY

In general, the invention is directed to techniques for evaluating a therapy delivered to a patient by a medical device based on patient activity, posture, or both. At any given time, the medical device delivers the therapy according to a current set of therapy parameters. The therapy parameters may be changed over time such that the therapy is delivered according to a plurality of different therapy parameter sets. The invention may provide techniques for evaluating the relative efficacy of the plurality of therapy parameter sets.

A system according to the invention may include a medical device that delivers therapy to a patient, one or more programmers or other computing devices that communicate with the medical device, and one or more sensors that generate signals as a function of at least one of patient activity and posture. The medical device, programmer, or other computing device may determine values of one or more activity metrics and, in some embodiments, may also determine posture metric values for each therapy parameter set used by the medical device to deliver therapy. The activity and posture metric values for a therapy parameter set are determined based on the signals generated by the sensors when that therapy parameter set was in use. The activity metric value may indicate a level of activity when the medical device used a particular therapy parameter set. Activity metric values may be associated with a postural category in addition to a therapy parameter set, and may indicate the duration and intensity of activity within one or more postural categories resulting from delivery of therapy according to a therapy parameter set. A posture metric value for a therapy parameter set may indicate the fraction of time spent by the patient in various postures when the medical device used a particular therapy parameter set.

The therapy and subsequent evaluation of therapy may be directed to treating any number of disorders. For example, the therapy may be directed to treating a non-respiratory neurological disorder, such as a movement disorder or psychological disorder. Example movement disorders for which therapy may be provided are Parkinson's disease, essential tremor and epilepsy. Non-respiratory neurological disorders do not include respiratory disorders, such as sleep apnea.

A clinician may use the one or more activity or posture metric values to evaluate therapy parameter sets used by the medical device to deliver therapy, or a sensitivity analysis may identify one or more potentially efficacious therapy parameter sets based on the metric values. In either case, the activity and/or posture metric values may be used to evaluate the relative efficacy of the parameter sets, and the parameter sets that support the highest activity levels and most upright and active postures for the patient may be readily identified.

In one embodiment, the invention is directed to a method in which a plurality of signals are monitored. Each of the signals is generated by a sensor as a function of at least one of activity or posture of a patient. A posture of the patient is periodically identified based on at least one of the signals, and each of the identified postures is associated with a therapy parameter set currently used by a medical device to deliver a therapy to a patient when the posture is identified. An activity level of the patient is periodically determined based on at least one of the signals, and each of the determined activity levels is associated with a therapy parameter set currently used by a medical device to deliver a therapy to a patient when the activity level is identified, and with a current one of the periodically identified postures. For each of a plurality of therapy parameter sets used by the medical device to deliver therapy to the patient, a value of an activity metric may be determined for each of the periodically identified postures associated with the therapy parameter set based on the activity levels associated with the posture and the therapy parameter set.

In another embodiment, the invention is directed to medical system comprising a plurality of sensors, each of the sensors generating a signal as a function of at least one of activity or posture of a patient, a medical device that delivers a therapy to the patient, and a processor. The processor monitors the signals generated by the sensors, periodically identifies a posture of the patient based on at least one of the signals, associates each of the identified postures with a therapy parameter set currently used by a medical device to deliver a therapy to a patient when the posture is identified, periodically determines an activity level of the patient based on at least one of the signals, associates each of the determined activity levels with a therapy parameter set currently used by a medical device to deliver a therapy to a patient when the activity level is determined and a current one of the periodically identified postures, and, for each of a plurality of therapy parameter sets used by the medical device to deliver therapy to the patient, determines a value of an activity metric for each of the periodically identified postures associated with the therapy parameter set based on the activity levels associated with the posture and the therapy parameter set.

In another embodiment, the invention is directed to a computer-readable medium comprising instructions. The instructions cause a programmable processor to monitor a plurality of signals, each of the signals generated by a sensor as a function of at least one of activity or posture of a patient. The instructions further cause the processor to periodically identify a posture of the patient based on at least one of the signals, and associate each of the identified postures with a therapy parameter set currently used by a medical device to deliver a therapy to a patient when the posture is identified. The instructions further cause the processor to periodically determine an activity level of the patient based on at least one of the signals, and associate each of the determined activity levels with a therapy parameter set currently used by a medical device to deliver a therapy to a patient when the activity level is determined and a current one of the periodically identified postures. The instructions further cause the processor to, for each of a plurality of therapy parameter sets used by the medical device to deliver therapy to the patient, determine a value of an activity metric for each of the periodically identified postures associated with the therapy parameter set based on the activity levels associated with the posture and the therapy parameter set.

The invention is capable of providing one or more advantages. For example, a medical system according to the invention may provide a clinician with an objective indication of the efficacy of different sets of therapy parameters. The indication of efficacy may be provided in terms of the ability of the patient to assume particular postures and activity levels for each given set of therapy parameters, permitting identification of particular sets of therapy parameters that yield the highest efficacy. Further, a medical device, programming device, or other computing device according to the invention may display therapy parameter sets and associated metric values in an ordered and, in some cases, sortable list, which may allow the clinician to more easily compare the relative efficacies of a plurality of therapy parameter sets. The medical system may be particularly useful in the context of trial neurostimulation for treatment of chronic pain or movement disorders, where the patient is encouraged to try a plurality of therapy parameter sets to allow the patient and clinician to identify efficacious therapy parameter sets. Further, in some embodiments, the system may provide at least semi-automated identification of potentially efficacious therapy parameter sets, through application of a sensitivity analysis to one or more activity or posture metrics.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 8 illustrates an example list of therapy parameter sets and associated posture and activity metric values that may be presented by a clinician programmer.

DETAILED DESCRIPTION

Figure 1A:
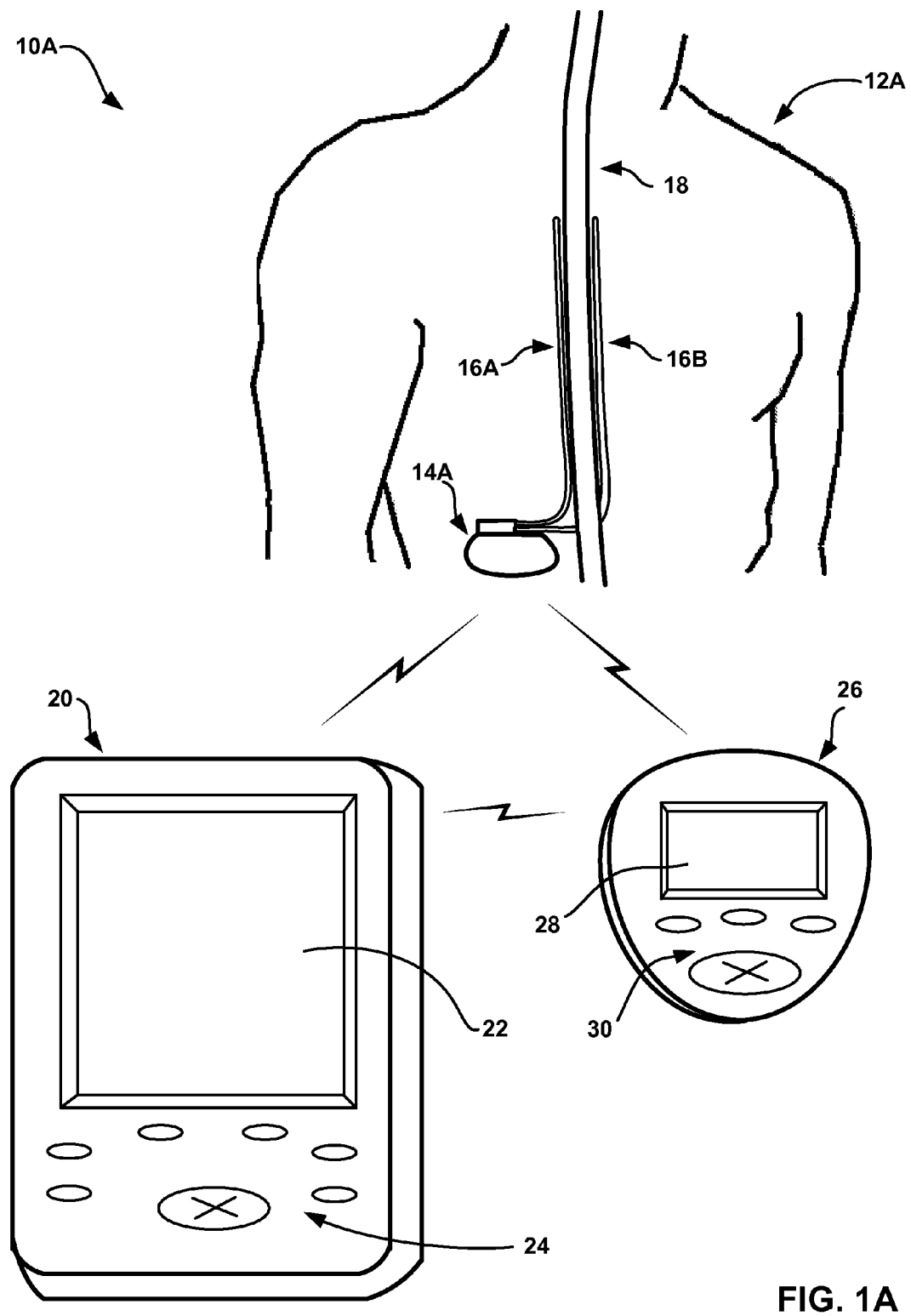
FIGS. 1A and 1B are conceptual diagrams illustrating example systems that include an implantable medical device that collects posture and activity information according to the invention.
Figure 1B:
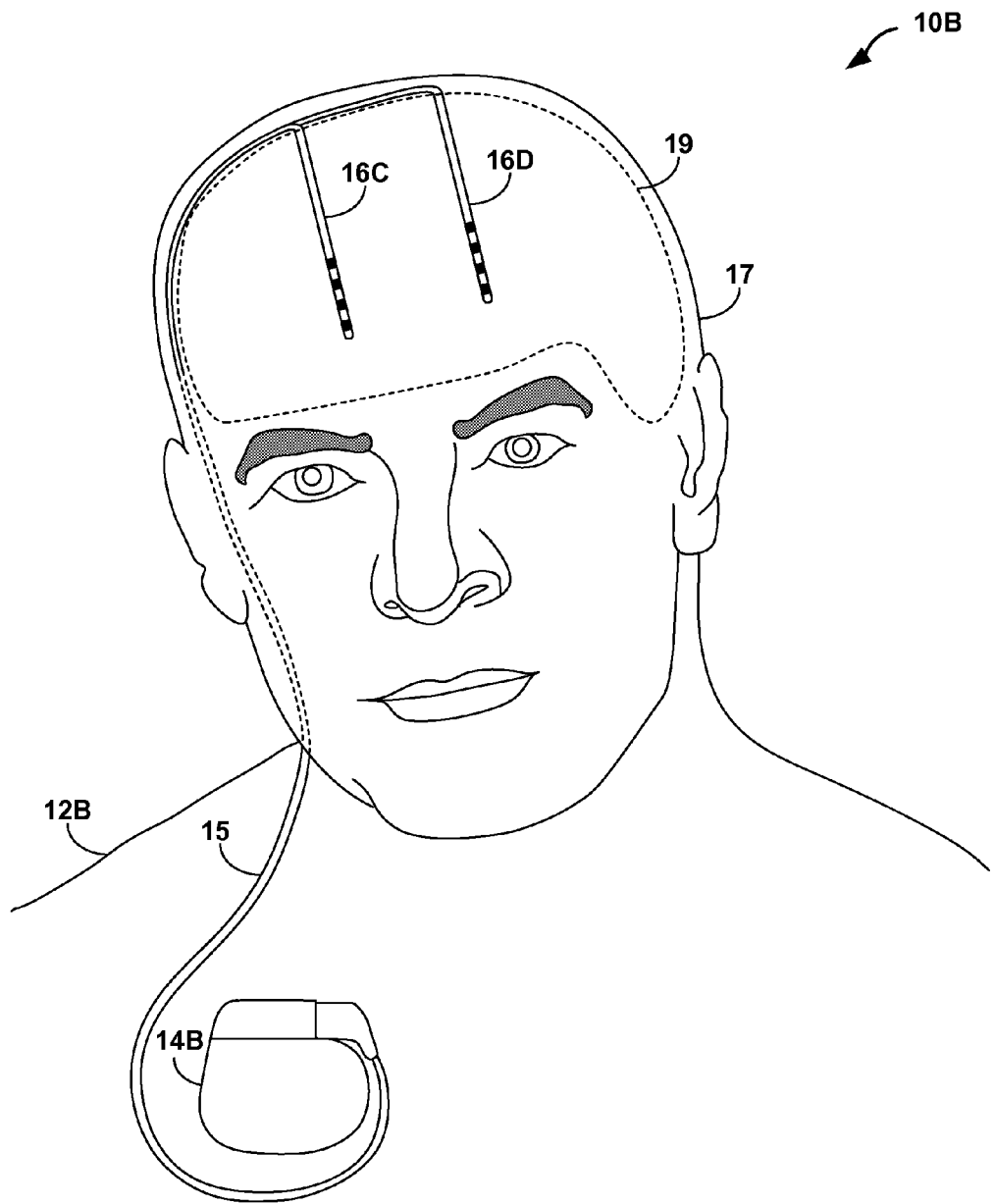

FIGS. 1A and 1B are conceptual diagrams illustrating example systems 10A and 10B (collectively "systems 10") that respectively include an implantable medical device (IMD) 14A or 14B (collectively "IMDs 14") that collect information relating to the activity and, in some embodiments, the posture of a respective one or patients 12A and 12B (collectively "patients 12"). In the illustrated example systems 10, IMDs 14 takes the form of an implantable neurostimulators that deliver neurostimulation therapy in the form of electrical pulses to patients 12. However, the invention is not limited to implementation via an implantable neurostimulator. For example, in some embodiments of the invention, IMDs 14 may take the form of an implantable pump or implantable cardiac rhythm management device, such as a pacemaker, that collects activity and posture information. Further, the invention is not limited to implementation via an IMD. In other words, any implantable or external medical device may collect activity and posture information according to the invention.

In the example of FIGS. 1A and 1B, IMDs 14 deliver neurostimulation therapy to patient 12A via leads 16A and 16B, and leads 16C and 16D (collectively "leads 16"), respectively. Leads 16A and 16B may, as shown in FIG. 1A, be implanted proximate to the spinal cord 18 of patient 12A, and IMD 14A may deliver spinal cord stimulation (SCS) therapy to patient 12A in order to, for example, reduce pain experienced by patient 12A. However, the invention is not limited to the configuration of leads 16A and 16B shown in FIG. 1A or the delivery of SCS or other pain therapies.

For example, in another embodiment, illustrated in FIG. 1B, leads 16C and 16D may extend to brain 19 of patient 12B, e.g., through cranium 17 of patient. IMD 14B may deliver deep brain stimulation (DBS) or cortical stimulation therapy to patient 12 to treat any of a variety of non-respiratory neurological disorders, such as movement disorders or psychological disorders. Example therapies may treat tremor, Parkinson's disease, spasticity, epilepsy, depression or obsessive-compulsive disorder. As illustrated in FIG. 1B, leads 16C and 16D may be coupled to IMD 14B via one or more lead extensions 15.

As further examples, one or more leads 16 may be implanted proximate to the pelvic nerves (not shown) or stomach (not shown), and an IMD 14 may deliver neurostimulation therapy to treat incontinence or gastroparesis. Additionally, leads 16 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain.

The illustrated numbers and locations of leads 16 are merely examples. Embodiments of the invention may include any number of leads implanted at any of a variety of locations within a patient. Furthermore, the illustrated number and location of IMDs 14 are merely examples. IMDs 14 may be located anywhere within patient according to various embodiments of the invention. For example, in some embodiments, an IMD 14 may be implanted on or within cranium 17 for delivery of therapy to brain 19, or other structure of the head of the patient 12.

IMDs 14 deliver therapy according to a set of therapy parameters, i.e., a set of values for a number of parameters that define the therapy delivered according to that therapy parameter set. In embodiments where IMDs 14 deliver neurostimulation therapy in the form of electrical pulses, the parameters in each parameter set may include voltage or current pulse amplitudes, pulse widths, pulse rates, duration, duty cycle and the like. Further, each of leads 16 includes electrodes (not shown in FIGS. 1A and 1B), and a therapy parameter set may include information identifying which electrodes have been selected for delivery of pulses, and the polarities of the selected electrodes. In embodiments in which IMDs 14 deliver other types of therapies, therapy parameter sets may include other therapy parameters such as drug concentration and drug flow rate in the case of drug delivery therapy. Therapy parameter sets used by IMDs 14 may include a number of parameter sets programmed by a clinician (not shown), and parameter sets representing adjustments made by patients 12 to these preprogrammed sets.

Each of systems 10 may also include a clinician programmer 20 (illustrated as part of system 10A in FIG. 1A). The clinician may use clinician programmer 20 to program therapy for patient 12A, e.g., specify a number of therapy parameter sets and provide the parameter sets to IMD 14A. The clinician may also use clinician programmer 20 to retrieve information collected by IMD 14A. The clinician may use clinician programmer 20 to communicate with IMD 14A both during initial programming of IMD 14A, and for collection of information and further programming during follow-up visits.

Clinician programmer 20 may, as shown in FIG. 1A, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

Systems 10 may also include a patient programmer 26 (illustrated as part of system 10A in FIG. 1A), which also may, as shown in FIG. 1A, be a handheld computing device. Patient 12A may use patient programmer 26 to control the delivery of therapy by IMD 14A. For example, using patient programmer 26, patient 12A may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12A to interact with patient programmer 26. In some embodiments, display 26 may be a touch screen display, and patient 12A may interact with patient programmer 26 via display 28. Patient 12A may also interact with patient programmer 26 using peripheral pointing devices, such as a stylus, mouse, or the like.

Clinician and patient programmers 20, 26 are not limited to the hand-held computer embodiments illustrated in FIG. 1A. Programmers 20, 26 according to the invention may be any sort of computing device. For example, a programmer 20, 26 according to the invention may be a tablet-based computing device, a desktop computing device, or a workstation.

IMD 14A, clinician programmer 20 and patient programmer 26 may, as shown in FIG. 1A, communicate via wireless communication. Clinician programmer 20 and patient programmer 26 may, for example, communicate via wireless communication with IMD 14A using radio frequency (RF) or infrared telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, an IMD 14 collects patient activity information. Specifically, as will be described in greater detail below, an IMD 14 periodically determines an activity level of a patient 12 based on a signal that varies as a function of patient activity. An activity level may comprise, for example, a number of activity counts, or a value for a physiological parameter that reflects patient activity.

In some embodiments, an IMD 14 also collects patient posture information. In such embodiments, an IMD 14 may monitor one or more signals that vary as a function of patient posture, and may identify postures based on the signals. An IMD 14 may, for example, periodically identify the posture of a patient 12 or transitions between postures made by the patient 12. For example, an IMD 14 may identify whether the patient is upright or recumbent, e.g., lying down, whether the patient is standing, sitting, or recumbent, or transitions between such postures.

In exemplary embodiments, as will be described in greater detail below, an IMD 14 monitors the signals generated by a plurality of accelerometers. In such embodiments, an IMD 14 may both determine activity levels and identify postures or postural transitions based on the accelerometer signals. Specifically, an IMD 14 may compare the DC components of the accelerometer signals to one or more thresholds to identify postures, and may compare a non-DC portion of one or more of the signals to one or more thresholds to determine activity levels.

Over time, an IMD 14 may use a plurality of different therapy parameter sets to deliver the therapy to a patient 12. In some embodiments, an IMD 14 associates each determined posture with the therapy parameter set that is currently active when the posture is identified. In such embodiments, an IMD 14 may also associate each determined activity level with the currently identified posture, and with the therapy parameter set that is currently active when the activity level is determined. In other embodiments, an IMD 14 may use posture to control whether activity levels are monitored. In such embodiments, an IMD 14 determines whether a patient 12 is in a target posture, e.g., a posture of interest such as upright or standing, and determines activity levels for association with current therapy parameter sets during periods when the patient is in the target posture.

In either case, an IMD 14 may determine at least one value of one or more activity metrics for each of the plurality of therapy parameter sets based on the activity levels associated with the therapy parameter sets. An activity metric value may be, for example, a mean or median activity level, such as an average number of activity counts per unit time. In other embodiments, an activity metric value may be chosen from a predetermined scale of activity metric values based on a comparison of a mean or median activity level to one or more threshold values. The scale may be numeric, such as activity metric values from 1-10, or qualitative, such as low, medium or high activity.

In some embodiments, each activity level associated with a therapy parameter set is compared with the one or more thresholds, and percentages of time above and/or below the thresholds are determined as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set.

In embodiments in which an IMD 14 associates identified postures with the current therapy parameter set, and associates each determined activity level with a current posture and the current therapy parameter set, the IMD 14 may, for each therapy parameter set, identify the plurality of postures assumed by a patient 12 when that therapy parameter set was in use. An IMD 14 may then determine a value of one or more activity metrics for each therapy parameter set/posture pair based on the activity levels associated with that therapy parameter set/posture pair.

Further, for each therapy parameter set, an IMD 14 may also determine a value of one or more posture metrics based on the postures or postural transitions associated with that therapy parameter set. A posture metric value may be, for example, an amount or percentage of time spent in a posture while a therapy parameter set is active, e.g., an average amount of time over a period of time, such as an hour, that a patient 12 was within a particular posture. In some embodiments, a posture metric value may be an average number of posture transitions over a period of time, e.g., an hour.

In some embodiments, a plurality of activity metric values are determined for each of the plurality of therapy parameter sets, or parameter set/posture pairs. In such embodiments, an overall activity metric value may be determined. For example, the plurality of individual activity metric values may be used as indices to identify an overall activity metric value from a look-up table. The overall activity metric may be selected from a predetermined scale of activity metric values, which may be numeric, such as activity metric values from 1-10, or qualitative, such as low, medium or high activity.

Similarly, in some embodiments, a plurality of posture metric values is determined for each of the plurality of therapy parameter sets. In such embodiments, an overall posture metric value may be determined. For example, the plurality of individual posture metric values may be used as indices to identify an overall posture metric value from a look-up table. The overall posture metric may be selected from a predetermined scale of posture metric values, which may be numeric, such as posture metric values from 1-10.

Although described herein primarily with reference to an IMD 14, one or more of the IMD 14, clinician programmer 20, patient programmer 26, or another computing device may determine activity and posture metric values in the manner described herein with reference to the IMD 14. For example, in some embodiments, an IMD 14 determines and stores metric values, and provides information identifying therapy parameter sets and the metric values associated with the therapy parameter sets, to one or both of programmers 20, 26. In other embodiments, an IMD 14 provides information identifying the therapy parameter sets and associated posture events and activity levels to one or both of programmers 20, 26, or another computing device, and the programmer or other computing device determines activity and posture metric values for each of the therapy parameter sets.

In either of these embodiments, programmers 20, 26 or the other computing device may present information to a user that may be used to evaluate the therapy parameter sets based on the activity and posture metric values. For ease of description, the presentation of information that may be used to evaluate therapy parameter sets will be described hereafter with reference to embodiments in which clinician programmer 20 presents information to a clinician. However, it is understood that, in some embodiments, patient programmer 26 or another computing device may present such information to a user, such as a clinician or a patient 12.

For example, in some embodiments, clinician programmer 20 may present a list of the plurality of parameter sets and associated posture and activity metric values to the clinician via display 22. Where values are determined for a plurality of posture and activity metrics for each of the therapy parameter sets, programmer 20 may order the list according to the values of one of the metrics that is selected by the clinician. Programmer 20 may also present other activity and/or posture information to the clinician, such as graphical representations of activity and/or posture. For example, programmer 20 may present a trend diagram of activity or posture over time, or a histogram or pie chart illustrating percentages of time that activity levels were within certain ranges or that a patient 12 assumed certain postures. Programmer 20 may generate such charts or diagrams using activity levels or posture events associated with a particular one of the therapy parameter sets, or all of the activity levels and posture events determined by an IMD 14.

However, the invention is not limited to embodiments that include programmers 20, 26 or another computing device, or embodiments in which a programmer or other computing device presents posture and activity information to a user. For example, in some embodiments, an external medical device comprises a display. In such embodiments, the external medical device both determines the metric values for the plurality of therapy parameter sets, and presents the list of therapy parameter sets and associated metric values.

Further, the invention is not limited to embodiments in which a medical device determines activity levels or identifies postures. For example, in some embodiments, an IMD 14 may instead periodically record samples of one or more signals, and associate the samples with a current therapy parameter set. In such embodiments, a programmer 20, 26 or another computing device may receive information identifying a plurality of therapy parameter sets and the samples associated with the parameter sets, determine activity levels and identify postures and postural transitions based on the samples, and determine one or more activity and/or posture metric values for each of the therapy parameter sets based on the determined activity levels and identified postures.

Moreover, the invention is not limited to embodiments in which the therapy delivering medical device includes or is coupled to the sensors that generate a signal as a function of patient activity or posture. In some embodiments, systems 10 may include a separate implanted or external monitor that includes or is coupled to such sensors. The monitor may provide samples of the signals generated by such sensors to the IMD, programmers or other computing device for determination of activity levels, postures, activity metric values and posture metric values as described herein.

The monitor may provide the samples in real-time, or may record samples for later transmission. In embodiments where the monitor records the samples for later transmission, the monitor may associate the samples with the time they were recorded. In such embodiments, an IMD 14 may periodically record indications of a currently used therapy parameter set and the current time. Based on the association of recorded signal samples and therapy parameter sets with time, the recorded signal samples may be associated with current therapy parameter sets for determination of activity and posture metric values as described herein.

In some embodiments, in addition to, or as an alternative to the presentation of information to a clinician for evaluation of therapy parameter sets, one or more of an IMD 14, programmers 20, 26, or another computing device may identify therapy parameter sets for use in delivery of therapy to a patient 12 based on a sensitivity analysis of one or more activity and/or posture metrics. The sensitivity analysis identifies values of therapy parameters that define a substantially maximum or minimum value of the one or more metrics. In particular, as will be described in greater detail below, one or more of an IMD 14 and programmers 20, 26 conducts the sensitivity analysis of the one or more metrics, and identifies at least one baseline therapy parameter set that includes the values for individual therapy parameters that were identified based on the sensitivity analysis. An IMD 14 may delivery therapy according to the baseline therapy parameter set. Furthermore, one or more of an IMD 14 and programmers 20, 26 may periodically perturb at least one therapy parameter value of the baseline therapy parameter set to determine whether the baseline therapy parameter set still defines a substantially maximum or minimum value of the one or more metrics. If the baseline therapy parameter set no longer defines a substantially maximum or minimum value of the one or more metrics, a search may be performed to identify a new baseline therapy parameter set for use in delivery of therapy to a patient 12.

Figure 2A:
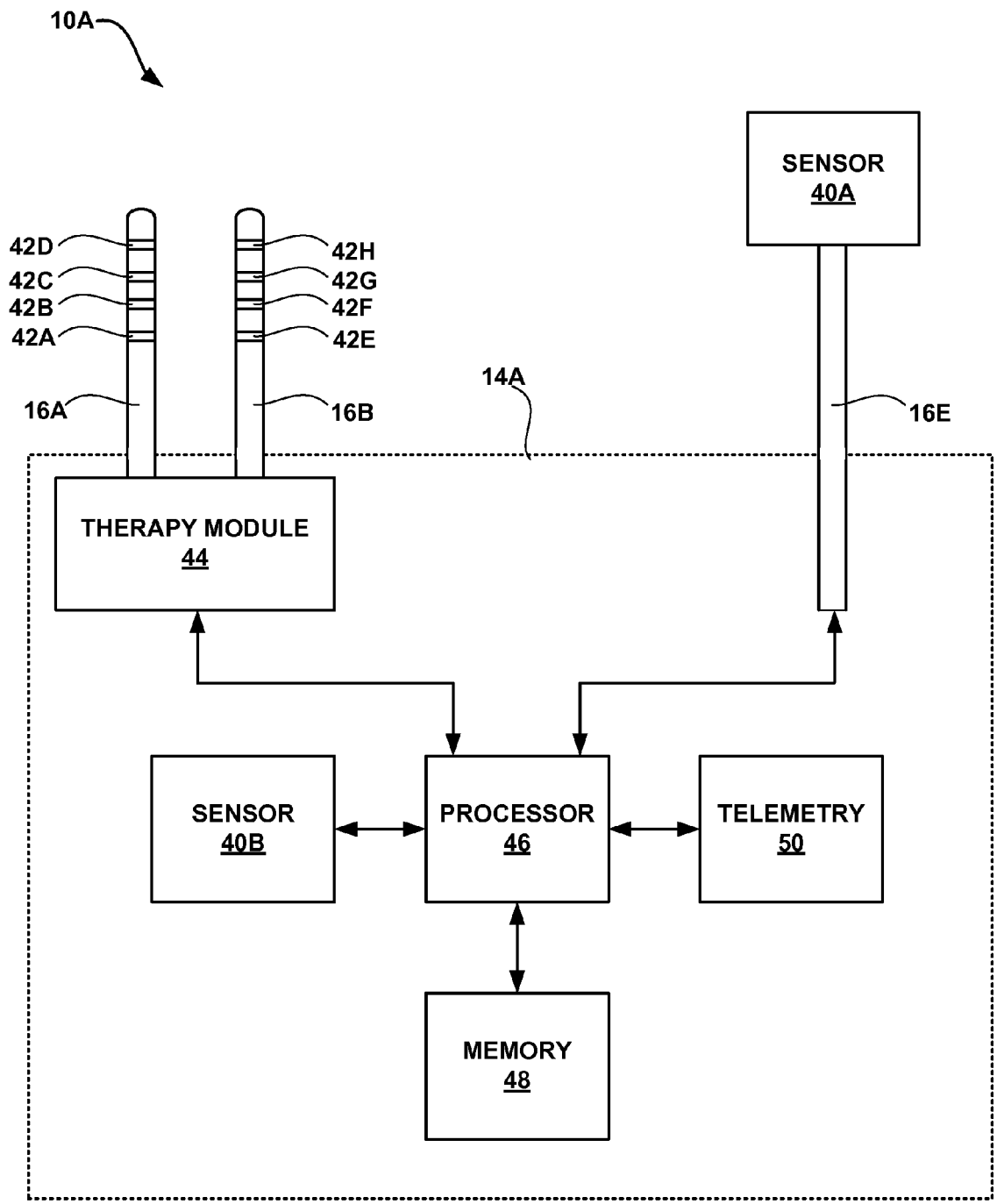
FIGS. 2A and 2B are block diagrams further illustrating the example systems and implantable medical devices of FIGS. 1A and 1B.
Figure 2B:
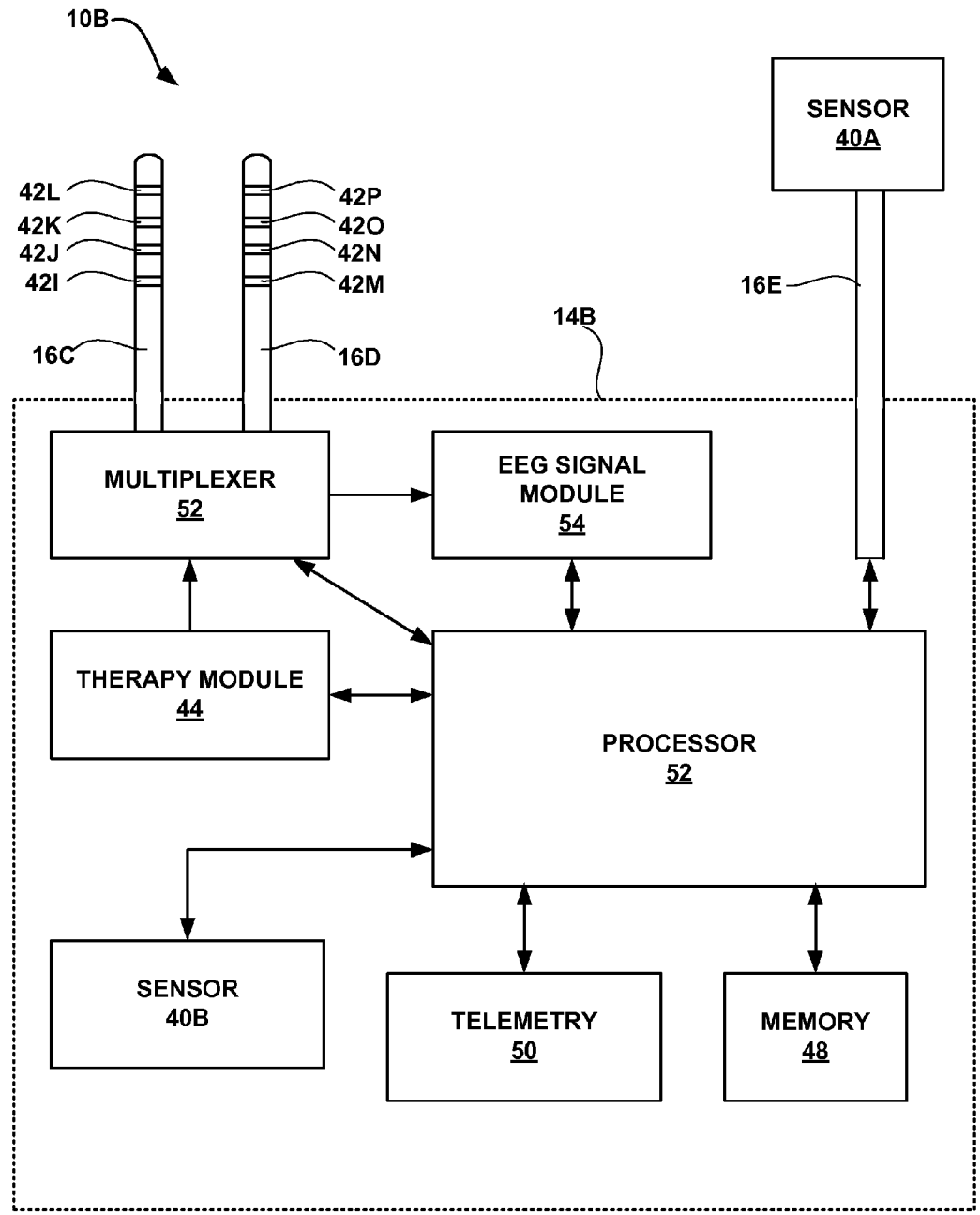

FIGS. 2A and 2B are block diagrams further illustrating systems 10A and 10B. In particular, FIG. 2A illustrates an example configuration of IMD 14A and leads 16A and 16B. FIG. 2B illustrates an example configuration of IMD 14B and leads 16C and 16D. FIGS. 2A and 2B also illustrate sensors 40A and 40B (collectively "sensors 40") that generate signals that vary as a function of patient activity and/or posture. As will be described in greater detail below, IMDs 14 monitor the signals, and may periodically identify the posture of patients 12 and determine an activity level based on the signals.

IMD 14A may deliver neurostimulation therapy via electrodes 42A-D of lead 16A and electrodes 42E-H of lead 16B, while IMD 14B delivers neurostimulation via electrodes 42I-L of lead 16C and electrodes 42 M-P of lead 16D (collectively "electrodes 40"). Electrodes 40 may be ring electrodes. The configuration, type and number of electrodes 40 illustrated in FIGS. 2A and 2B are merely exemplary. For example, leads 16 may each include eight electrodes 40, and the electrodes 42 need not be arranged linearly on each of leads 16.

In each of systems 10A and 10B, electrodes 42 are electrically coupled to a therapy delivery module 44 via leads 16. Therapy delivery module 44 may, for example, include an output pulse generator coupled to a power source such as a battery. Therapy delivery module 44 may deliver electrical pulses to a patient 12 via at least some of electrodes 42 under the control of a processor 46, which controls therapy delivery module 44 to deliver neurostimulation therapy according to a current therapy parameter set. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal that varies as a function of patient activity and/or posture. An IMD 14 may include circuitry (not shown) that conditions the signals generated by sensors 40 such that they may be analyzed by processor 46. For example, an IMD 14 may include one or more analog to digital converters to convert analog signals generated by sensors 40 into digital signals usable by processor 46, as well as suitable filter and amplifier circuitry. Although shown as including two sensors 40, systems 10A and 10B may include any number of sensors.

Further, as illustrated in FIGS. 2A and 2B, sensors 40 may be included as part of IMDs 14, or coupled to IMDs 14 via leads 16. Sensors 40 may be coupled to IMD 14 via therapy leads 16A-16D, or via other leads 16, such as lead 16E depicted in FIGS. 2A and 2B. In some embodiments, a sensor 40 located outside of an IMD 14 may be in wireless communication with processor 46. Wireless communication between sensors 40 and IMDs 14 may, as examples, include RF communication or communication via electrical signals conducted through the tissue and/or fluid of a patient 12.

In exemplary embodiments, sensors 40 include a plurality of accelerometers, e.g., three accelerometers, which are oriented substantially orthogonally with respect to each other. In addition to being oriented orthogonally with respect to each other, each of accelerometers may be substantially aligned with an axis of the body of a patient 12. The magnitude and polarity of DC components of the signals generated by the accelerometers indicate the orientation of the patient relative to the Earth's gravity, and processor 46 may periodically identify the posture or postural changes of a patient 12 based on the magnitude and polarity of the DC components. Further information regarding use of orthogonally aligned accelerometers to determine patient posture may be found in a commonly assigned U.S. Pat. No. 5,593,431, which issued to Todd J. Sheldon.

Processor 46 may periodically determine the posture of a patient 12, and may store indications of the determined postures within memory 48. Where a system 10 includes a plurality of orthogonally aligned accelerometers located on or within the trunk of a patient 12, e.g., within an IMD 14 which is implanted within the abdomen of the patient 12 as illustrated in FIGS. 1A and 1B, processor 46 may be able to periodically determine whether patient is, for example, upright or recumbent, e.g., lying down. In embodiments of systems 10 that include an additional one or more accelerometers at other locations on or within the body of a patient 12, processor 46 may be able to identify additional postures of the patient 12. For example, in an embodiment of systems 10 that includes one or more accelerometers located on or within the thigh of a patient 12, processor 46 may be able to identify whether the patient 12 is standing, sitting, or lying down. Processor 46 may also identify transitions between postures based on the signals output by the accelerometers, and may store indications of the transitions, e.g., the time of transitions, within memory 48.

Processor 46 may identify postures and posture transitions by comparing the signals generated by the accelerometers to one or more respective threshold values. For example, when a patient 12 is upright, a DC component of the signal generated by one of the plurality of orthogonally aligned accelerometers may be substantially at a first value, e.g., high or one, while the DC components of the signals generated by the others of the plurality of orthogonally aligned accelerometers may be substantially at a second value, e.g., low or zero. When a patient 12 becomes recumbent, the DC component of the signal generated by one of the plurality of orthogonally aligned accelerometers that had been at the second value when the patient was upright may change to the first value, and the DC components of the signals generated by others of the plurality of orthogonally aligned accelerometers may remain at or change to the second value. Processor 46 may compare the signals generated by such sensors to respective threshold values stored in memory 48 to determine whether they are substantially at the first or second value, and to identify when the signals change from the first value to the second value.

Processor 46 may determine an activity level based on one or more of the accelerometer signals by sampling the signals and determining a number of activity counts during the sample period. For example, processor 46 may compare the sample of a signal generated by an accelerometer to one or more amplitude thresholds stored within memory 48, and may identify each threshold crossing as an activity count. Where processor 46 compares the sample to multiple thresholds with varying amplitudes, processor 46 may identify crossing of higher amplitude thresholds as multiple activity counts. Using multiple thresholds to identify activity counts, processor 46 may be able to more accurately determine the extent of patient activity for both high impact, low frequency and low impact, high frequency activities. Processor 46 may store the determined number of activity counts in memory 48 as an activity level. In some embodiments, an IMD 14 may include a filter (not shown), or processor 46 may apply a digital filter, that passes a band of the accelerometer signal from approximately 0.1 Hz to 10 Hz, e.g., the portion of the signal that reflects patient activity.

Processor 46 may identify postures and record activity levels continuously or periodically, e.g., one sample of the signals output by sensors 40 every minute or continuously for ten minutes each hour. Further, processor 46 need not identify postures and record activity levels with the same frequency. For example, processor 46 may identify postures less frequently then activity levels are determined.

In some embodiments, processor 46 limits recording of postures and activity levels to relevant time periods, i.e., when a patient 12 is awake or likely to be awake, and therefore likely to be active. For example, a patient 12 may indicate via patient programmer 26 when patient is going to sleep or has awoken. Processor 46 may receive these indications via a telemetry circuit 50 of an IMD 14, and may suspend or resume recording of posture events based on the indications. In other embodiments, processor 46 may maintain a real-time clock, and may record posture events based on the time of day indicated by the clock, e.g., processor 46 may limit posture event recording to daytime hours. Alternatively, processor 46 may wirelessly interact with a real-time clock within the patient programmer.

In some embodiments, processor 46 may monitor one or more physiological parameters of a patient 12 via signals generated by sensors 40, and may determine when the patient 12 is attempting to sleep or asleep based on the physiological parameters. For example, processor 46 may determine when a patient 12 is attempting to sleep by monitoring the posture of the patient 12 to determine when the patient 12 is recumbent.

In order to determine whether a patient 12 is asleep, processor 46 may monitor any one or more physiological parameters that discernibly change when the patient 12 falls asleep, such as activity level, heart rate, ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response. Processor 46 may additionally or alternatively monitor the variability of one or more of these physiological parameters, such as heart rate and respiration rate, which may discernible change when a patient 12 is asleep. Further details regarding monitoring physiological parameters to identify when a patient is attempting to sleep and when the patient is asleep may be found in a commonly-assigned U.S. patent application Ser. No. 11/691,405 by Kenneth Heruth and Keith Miesel, entitled "DETECTING SLEEP," which was filed Mar. 26, 2007, issued as U.S. Pat. No. 8,055,348 on Nov. 8, 2011, and is incorporated herein by reference in its entirety.

In some embodiments, processor 46 gates activity and posture monitoring based on patient sleep. Further, in some embodiments, sensors 40 may include one or more electrodes positioned within or proximate to the brain of patient 12, which detect electrical activity of the brain. For example, in embodiments in which an IMD 14 delivers stimulation or therapeutic agents to the brain, processor 46 may be coupled to electrodes implanted on or within the brain via a lead 16. System 10B, illustrated in FIGS. 1B and 2B, is an example of a system that includes electrodes 42, located on or within the brain of patient 12B, that are coupled to IMD 14B.

As shown in FIG. 2B, electrodes 42 may be selectively coupled to therapy module 44 or an EEG signal module 54 by a multiplexer 52, which operates under the control of processor 46. EEG signal module 54 receives signals from a selected set of the electrodes 42 via multiplexer 52 as controlled by processor 46. EEG signal module 54 may analyze the EEG signal for certain features indicative of sleep or different sleep states, and provide indications of relating to sleep or sleep states to processor 46. Thus, electrodes 42 and EEG signal module 54 may be considered another sensor 40 in system 10B. IMD 14B may include circuitry (not shown) that conditions the EEG signal such that it may be analyzed by processor 52. For example, IMD 14B may include one or more analog to digital converters to convert analog signals received from electrodes 42 into digital signals usable by processor 46, as well as suitable filter and amplifier circuitry.

In some embodiments, processor 46 will only request EEG signal module 54 to operate when one or more other physiological parameters indicate that patient 12B is already asleep. However, processor 46 may also direct EEG signal module to analyze the EEG signal to determine whether patient 12B is sleeping, and such analysis may be considered alone or in combination with other physiological parameters to determine whether patient 12B is asleep. EEG signal module 60 may process the EEG signals to detect when patient 12 is asleep using any of a variety of techniques, such as techniques that identify whether a patient is asleep based on the amplitude and/or frequency of the EEG signals. In some embodiments, the functionality of EEG signal module 54 may be provided by processor 46, which, as described above, may include one or more microprocessors, ASICs, or the like.

In other embodiments, processor 46 may record postures and activity levels in response to receiving an indication from a patient 12 via patient programmer 26. For example, processor 46 may record postures and activity levels during times when a patient 12 believes the therapy delivered by an IMD 14 is ineffective and/or the symptoms experienced by the patient 12 have worsened. In this manner, processor 46 may limit data collection to periods in which more probative data is likely to be collected, and thereby conserve a battery and/or storage space within memory 48.

Although described above with reference to an exemplary embodiment in which sensors 40 include accelerometers, sensors 40 may include any of a variety of types of sensors that generate signals as a function of patient posture and/or activity. For example, sensors 40 may include orthogonally aligned gyros or magnetometers that generate signals that indicate the posture of a patient 12.

Other sensors 40 that may generate a signal that indicates the posture of a patient 12 include electrodes that generate an electromyogram (EMG) signal, or bonded piezoelectric crystals that generate a signal as a function of contraction of muscles. Such sensors 40 may be implanted in the legs, buttocks, abdomen, or back of a patient 12, as described above. The signals generated by such sensors when implanted in these locations may vary based on the posture of a patient 12, e.g., may vary based on whether the patient is standing, sitting, or lying down.

Further, the posture of a patient 12 may affect the thoracic impedance of the patient. Consequently, sensors 40 may include an electrode pair, including one electrode integrated with the housing of an IMD 14 and one of electrodes 42, that generates a signal as a function of the thoracic impedance of a patient 12, and processor 46 may detect the posture or posture changes of the patient 12 based on the signal. The electrodes of the pair may be located on opposite sides of the patient's thorax. For example, the electrode pair may include one of electrodes 42 located proximate to the spine of a patient for delivery of SCS therapy, and an IMD 14 with an electrode integrated in its housing may be implanted in the abdomen of a patient 12.

Additionally, changes of the posture of a patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to an IMD 14 wirelessly or via leads 16. CSF pressure changes associated with posture changes may be particularly evident within the brain of the patient, e.g., may be particularly apparent in an intracranial pressure (ICP) waveform.

Other sensors 40 that output a signal as a function of patient activity may include one or more bonded piezoelectric crystals, mercury switches, or gyros that generate a signal as a function of body motion, footfalls or other impact events, and the like. Additionally or alternatively, sensors 40 may include one or more electrodes that generate an electromyogram (EMG) signal as a function of muscle electrical activity, which may indicate the activity level of a patient. The electrodes may be, for example, located in the legs, abdomen, chest, back or buttocks of a patient 12 to detect muscle activity associated with walking, running, or the like. The electrodes may be coupled to an IMD 14 wirelessly or by leads 16 or, if the IMD 14 is implanted in these locations, integrated with a housing of the IMD 14.

However, bonded piezoelectric crystals located in these areas generate signals as a function of muscle contraction in addition to body motion, footfalls or other impact events. Consequently, use of bonded piezoelectric crystals to detect activity of a patient 12 may be preferred in some embodiments in which it is desired to detect muscle activity in addition to body motion, footfalls, or other impact events. Bonded piezoelectric crystals may be coupled to an IMD 14 wirelessly or via leads 16, or piezoelectric crystals may be bonded to the can of the IMD 14 when the IMD is implanted in these areas, e.g., in the back, chest, buttocks or abdomen of a patient 12.

Further, in some embodiments, processor 46 may monitor one or more signals that indicate a physiological parameter of a patient 12, which in turn varies as a function of patient activity. For example, processor 46 may monitor a signal that indicates the heart rate, ECG morphology, respiration rate, respiratory volume, core or subcutaneous temperature, or muscular activity of the patient, and sensors 40 may include any known sensors that output a signal as a function of one or more of these physiological parameters. In such embodiments, processor 46 may periodically determine a heart rate, value of an ECG morphological feature, respiration rate, respiratory volume, core temperature, or muscular activity level of a patient 12 based on the signal. The determined values of these parameters may be mean or median values.

In some embodiments, processor 46 compares a determined value of such a physiological parameter to one or more thresholds or a look-up table stored in memory to determine a number of activity counts, and stores the determined number of activity counts in memory 48 as a determined activity level. In other embodiments, processor 46 may store the determined physiological parameter value as a determined activity level. The use of activity counts, however, may allow processor 46 to determine an activity level based on a plurality of signals generated by a plurality of sensors 40. For example, processor 46 may determine a first number of activity counts based on a sample of an accelerometer signal and a second number of activity counts based on a heart rate determined from an electrogram signal at the time the accelerometer signal was sampled. Processor 46 may determine an activity level by calculating the sum or average, which may be a weighted sum or average, of first and second activity counts.

As described above, the invention is not limited to embodiments in which an IMD 14 determines postures or activity levels. In some embodiments, processor 46 may periodically store samples of the signals generated by sensors 40 in memory 48, rather than postures and activity levels, and may associate those samples with the current therapy parameter set.

Figure 3:
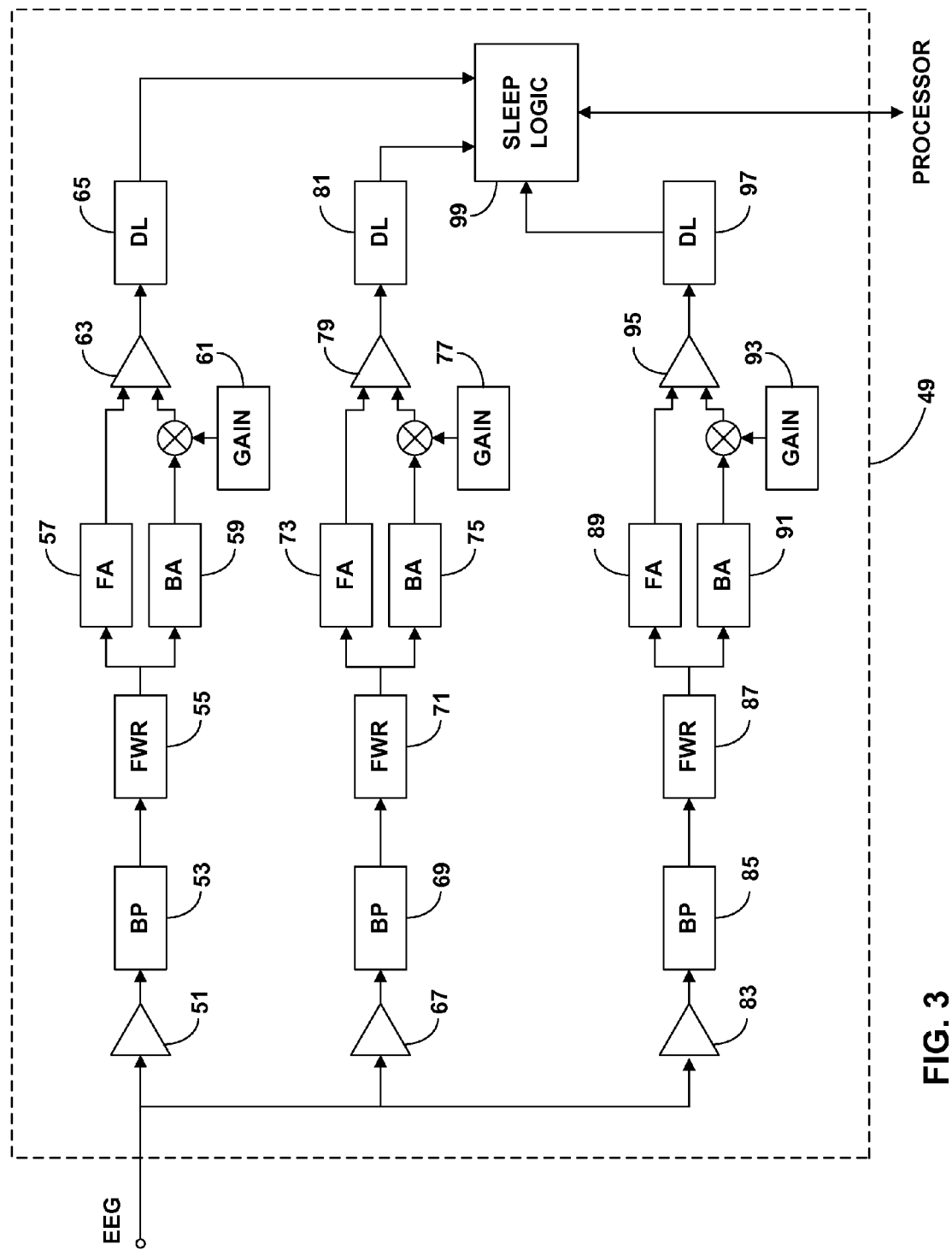
FIG. 3 is a logic diagram illustrating an example circuit that detects the sleep state of a patient from the electroencephalogram (EEG) signal.

FIG. 3 is a logical diagram of an example circuit that detects the sleep and/or sleep type of a patient based on the electroencephalogram (EEG) signal. Module 49, shown in FIG. 3, may be integrated into an EEG signal module 54 of IMD 14B, or some other implantable or external device capable of detecting an EEG signal according to other embodiments of the invention. In such embodiments, module 49 may be used to, for example, determine whether a patient 12 is asleep, or in which sleep state the patient is.

An EEG signal detected by electrodes 42 adjacent to the brain 19 of patent 12B is transmitted into module 49 and provided to three channels, each of which includes a respective one of amplifiers 51, 67 and 83, and bandpass filters 53, 69 and 85. In other embodiments, a common amplifier amplifies the EEG signal prior to filters 53, 69 and 85. Bandpass filter 53 allows frequencies between approximately 4 Hz and approximately 8 Hz, and signals within the frequency range may be prevalent in the EEG during S1 and S2 sleep states. Bandpass filter 69 allows frequencies between approximately 1 Hz and approximately 3 Hz, which may be prevalent in the EEG during the S3 and S4 sleep states. Bandpass filter 85 allows frequencies between approximately 10 Hz and approximately 50 Hz, which may be prevalent in the EEG during REM sleep. Each resulting signal may then processed to identify in which sleep state patient 12B is in.

After bandpass filtering of the original EEG signal, the filtered signals are similarly processed in parallel before being delivered to sleep logic module 99. For ease of discussion, only one of the three channels will be discussed herein, but each of the filtered signals may be processed similarly.

Once the EEG signal is filtered by bandpass filter 53, the signal is rectified by full-wave rectifier 55. Modules 57 and 59 respectively determine the foreground average and background average so that the current energy level can be compared to a background level at comparator 63. The signal from background average is increased by gain 61 before being sent to comparator 63, because comparator 63 operates in the range of millivolts or volts while the EEG signal amplitude is originally on the order of microvolts. The signal from comparator 63 is indicative of sleep stages S1 and S2. If duration logic 65 determines that the signal is greater than a predetermined level for a predetermined amount of time, the signal is sent to sleep logic module 99 indicating that patient 12 may be within the S1 or S2 sleep states. In some embodiments, as least duration logic 65, 81, 97 and sleep logic 99 may be embodied in a processor of the device containing EEG module 49.

Module 49 may detect all sleep types for patient 12. Further, the beginning of sleep may be detected by module 49 based on the sleep state of patient 12. Some of the components of module 49 may vary from the example of FIG. 3. For example, gains 61, 77 and 93 may be provided from the same power source. Module 49 may be embodied as analog circuitry, digital circuitry, or a combination thereof In other embodiments, module 49 may not need to reference the background average to determine the current state of sleep of patient 12. Instead, the power of the signals from bandpass filters 53, 69 and 85 are compared to each other, and sleep logic module 99 determines which the sleep state of patient 12 based upon the frequency band that has the highest power. In this case, the signals from full-wave rectifiers 55, 71 and 87 are sent directly to a device that calculates the signal power, such as a spectral power distribution module (SPD), and then to sleep logic module 99 which determines the frequency band of the greatest power, e.g., the sleep state of patient 12B. In some cases, the signal from full-wave rectifiers 55, 71 and 87 may be normalized by a gain component to correctly weight each frequency band.

Figure 4:
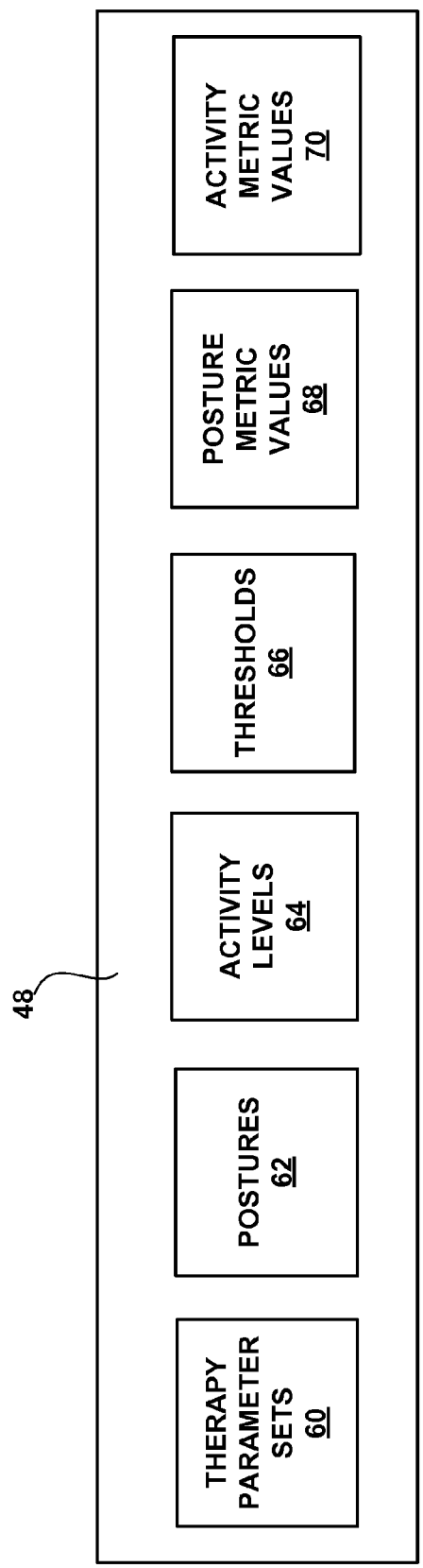
FIG. 4 is a block diagram illustrating an example memory of the implantable medical device of FIG. 1.

FIG. 4 illustrates memory 48 of IMDs 14 in greater detail. As shown in FIG. 4, memory 48 stores information describing a plurality of therapy parameter sets 60. Therapy parameter sets 60 may include parameter sets specified by a clinician using clinician programmer 20. Therapy parameter sets 60 may also include parameter sets that are the result of a patient 12 changing one or more parameters of one of the preprogrammed therapy parameter sets. For example, a patient 12 may change parameters such as pulse amplitude, frequency or pulse width.

Memory 48 also stores postures 62 or postural transitions identified by processor 46. When processor 46 identifies a posture 62 or postural transition as discussed above, processor 46 associates the posture or postural transition with the current one of therapy parameter sets 60, e.g., the one of therapy parameter sets 60 that processor 46 is currently using to control delivery of therapy by therapy module 44 to a patient 12. For example, processor 46 may store determined postures 62 within memory 48 with an indication of the parameter sets 60 with which they are associated. In other embodiments, processor 46 stores samples (not shown) of signals generated by sensors 40 as a function of posture within memory 48 with an indication of the parameter sets 60 with which they are associated.

Memory 48 also stores the activity levels 64 determined by processor 46. When processor 46 determines an activity level as discussed above, processor 46 associates the determined activity level 64 with the current therapy parameter set 60, e.g., the one of therapy parameter sets 60 that processor 46 is currently using to control delivery of therapy by therapy module 44 to a patient 12. In some embodiments, for example, processor 46 may store determined activity levels 64 within memory 48 with an indication of the posture 62 and parameter sets 60 with which they are associated. In other embodiments, processor 46 stores samples (not shown) of signals generated by sensors 40 as a function of patient activity within memory 48 with an indication of the posture 62 and parameter sets 60 with which they are associated.

In some embodiments, processor 46 determines a value of one or more activity metrics for each of therapy parameter sets 60 based on the activity levels 64 associated with the parameter sets 60. In such embodiments, processor 46 may store the determined activity metric values 70 within memory 48 with an indication as to which of therapy parameter sets 60 the determined values are associated with. For example, processor 46 may determine a mean or median of activity levels associated with a therapy parameter set, and store the mean or median activity level as an activity metric value 70 for the therapy parameter set.

In embodiments in which activity levels 64 comprise activity counts, processor 46 may store, for example, an average number of activity counts per unit time as an activity metric value. An average number of activity counts over some period substantially between ten and sixty minutes, for example, may provide a more accurate indication of activity than an average over shorter periods by ameliorating the effect of transient activities on an activity signal or physiological parameters. For example, rolling over in bed may briefly increase the amplitude of an activity signal and a heart rate, possibly skewing the efficacy analysis.

In other embodiments, processor 46 may compare a mean or median activity level to one or more threshold values, and may select an activity metric value from a predetermined scale of activity metric values based on the comparison. The scale may be numeric, such as activity metric values from 1-10, or qualitative, such as low, medium or high activity. The scale of activity metric values may be, for example, stored as a look-up table within memory 48. Processor 46 stores the activity metric value 70 selected from the scale within memory 48.

In some embodiments, processor 46 compares each activity level 64 associated with a therapy parameter set 60 to one or more threshold values. Based on the comparison, processor 46 may determine percentages of time above and/or below the thresholds, or within threshold ranges. Processor 46 may store the one or more determined percentages within memory 48 as one or more activity metric values 70 for that therapy parameter set. In other embodiments, processor 46 compares each activity level 64 associated with a therapy parameter set 60 to a threshold values, and determines an average length of time that consecutively recorded activity levels 64 remained above the threshold as an activity metric value 70 for that therapy parameter set.

In some embodiments, processor 46 determines a plurality of activity metric values for each of the plurality of therapy parameter sets, and determines an overall activity metric value for a parameter set based on the values of the individual activity metrics for that parameter set. For example, processor 46 may use the plurality of individual activity metric values as indices to identify an overall activity metric value from a look-up table stored in memory 48. Processor 46 may select the overall metric value from a predetermined scale of activity metric values, which may be numeric, such as activity metric values from 1-10, or qualitative, such as low, medium or high activity.

Further, as discussed above, processor 46 may identify the plurality of postures assumed by a patient 12 over the times that a therapy parameter set was active based on the postures 62 associated with that therapy parameter set. In such embodiments, processor 46 may determine a plurality of values of an activity metric for each therapy parameter set and posture, e.g., a value of the activity metric for each parameter set/posture pair. Processor 46 may determine an activity metric value 70 for a parameter set/posture pair based on the activity levels 64 associated with the therapy parameter set and the posture, e.g., the activity levels 64 collected while that therapy parameter set was active and the a patient 12 was in that posture.

In some embodiments, processor 46 also determines a value of one or more posture metrics for each of therapy parameter sets 60 based on the postures 62 associated with the parameter sets 60. Processor 46 may store the determined posture metric values 68 within memory 48 with an indication as to which of therapy parameter sets 60 the determined values are associated with. For example, processor 46 may determine an amount of time that a patient 12 was in a posture when a therapy parameter set 60 was active, e.g., an average amount of time over a period of time such as an hour, as a posture metric 68 for the therapy parameter set 60. Processor 46 may additionally or alternatively determine percentages of time that a patient 12 assumed one or more postures while a therapy parameter set was active as a posture metric 68 for the therapy parameter set 60. As another example, processor 46 may determine an average number of transitions over a period of time, such as an hour, when a therapy parameter set 60 was active as a posture metric 68 for the therapy parameter set 60.

In some embodiments, processor 46 determines a plurality of posture metric values for each of the plurality of therapy parameter sets 60, and determines an overall posture metric value for a parameter set based on the values of the individual posture metrics for that parameter set. For example, processor 46 may use the plurality of individual posture metric values as indices to identify an overall posture metric value from a look-up table stored in memory 48. Processor 46 may select the overall posture metric value from a predetermined scale of posture metric values, which may be numeric, such as posture metric values from 1-10.

The various thresholds described above as being used by processor 46 to determine activity levels 62, postures 64, posture metric values 68, and activity metric values 70 may be stored in memory 48 as thresholds 66, as illustrated in FIG. 4. In some embodiments, threshold values 66 may be programmable by a user, e.g., a clinician, using one of programmers 20, 26. Further, the clinician may select which activity metric values 70 and posture metric values 68 are to be determined via one of programmers 20, 26.

As shown in FIGS. 2A and 2B, IMDs 14 include a telemetry circuit 50, and processor 46 communicates with programmers 20, 26, or another computing device, via telemetry circuit 50. In some embodiments, processor 46 provides information identifying therapy parameter sets 60, postures 62, posture metric values 68, and activity metric values 70 associated with the parameter sets to one of programmers 20, 26, or the other computing device, and the programmer or other computing device displays a list of therapy parameter sets 60 and associated postures 62 and metric values 68, 70. In other embodiments, as will be described in greater detail below, processor 46 does not determine metric values 68, 70. Instead, processor 46 provides postures 62 and activity levels 64 to the programmer 20, 26 or other computing device via telemetry circuit 50, and the programmer or computing device determines metric values 68, 70 for display to the clinician. Further, in other embodiments, processor 46 provides samples of signals generated by sensors 40 to the programmer 20, 26 or other computing device via telemetry circuit 50, and the programmer or computing device may determine postures 62, activity levels 64, and metric values 68, 70 based on the samples. Some external medical device embodiments of the invention include a display, and a processor of such an external medical device may both determine metric values 68, 70 and display a list of therapy parameter sets 60 and associated metric values to a clinician.

Figure 5:
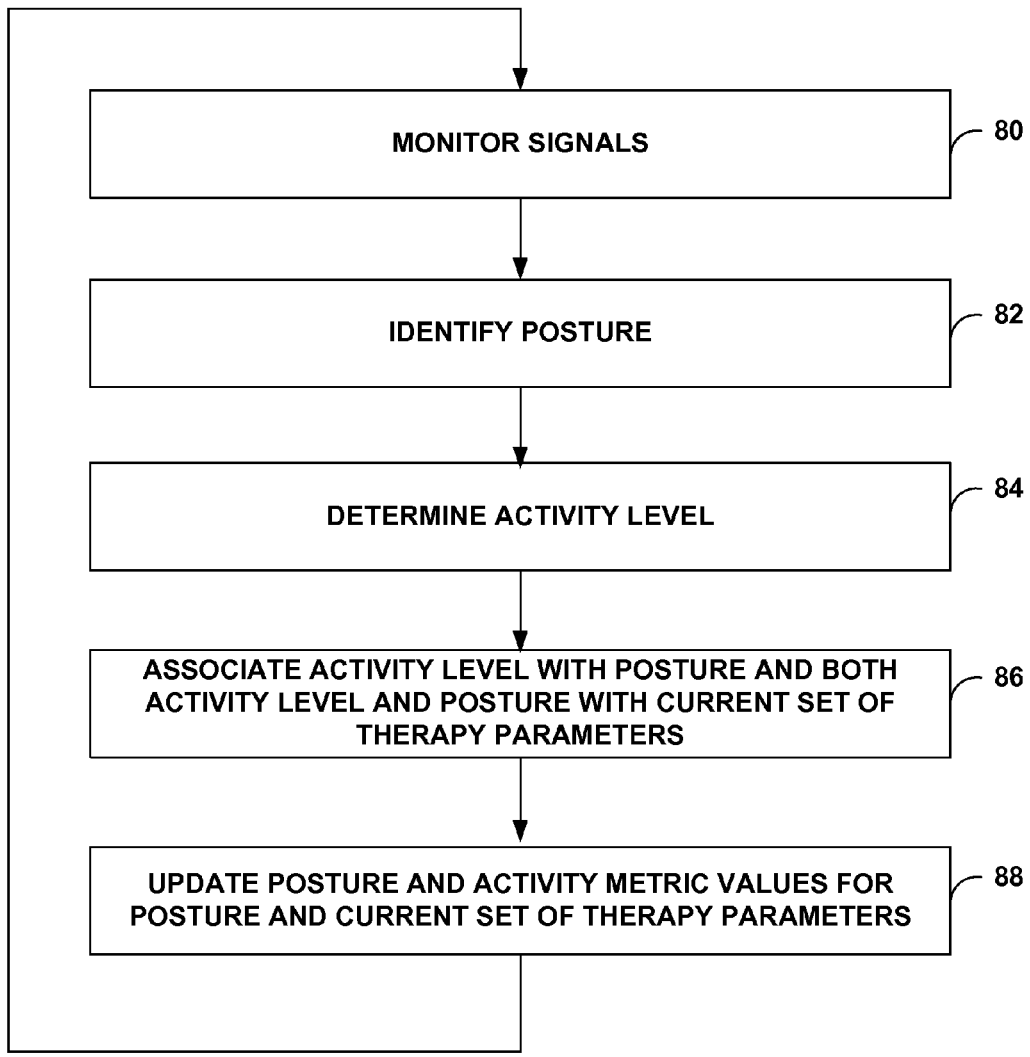
FIG. 5 is a flow diagram illustrating an example method for collecting posture and activity information that may be employed by an implantable medical device.

FIG. 5 is a flow diagram illustrating an example method for collecting posture and activity information that may be employed by an IMD 14. An IMD 14 monitors one or more signals generated by sensors 40 (80). For example, an IMD 14 may monitor signals generated by a plurality of orthogonally aligned accelerometers, as described above. Each of the accelerometers may be substantially aligned with a respective axis of the body of a patient 12.

An IMD 14 identifies a posture 62 (82). For example, the IMD 14 may identify a current posture of a patient 12 at a time when the signals generated by sensors 40 are sampled, or may identify the occurrence of a transition between postures. The IMD 14 also determines an activity level 64 (84). For example, the IMD 14 may determine a number of activity counts based on the one or more of the accelerometer signals, as described above.

An IMD 14 identifies the current therapy parameter set 60, and associates the identified posture 62 with the current therapy parameter set 60 (86). For example, an IMD 14 may store information describing the identified posture 62 within memory 48 with an indication of the current therapy parameter set 60. An IMD 14 also associates the determined activity level 64 with the posture a patient 12 is currently in, e.g., the most recently identified posture 62, and the current therapy parameter set 60 (86). For example, an IMD 14 may store the determined activity level 64 in memory 48 with an indication of the current posture 62 and therapy parameter set 60. An IMD 14 may then update one or more posture and/or activity metric values 68, 70 associated with the current therapy parameter set 60 and posture 62, e.g., the current therapy parameter set/posture pair, as described above (88).

An IMD 14 may periodically perform the example method illustrated in FIG. 5, e.g., may periodically monitor the signals generated by sensors 40 (80), determine postures 62 and activity levels 64 (82, 84), and associate the determined postures 62 and activity levels 64 with a current therapy parameter set 60 (86). Postures 62 and activity levels 64 need not be determined with the same frequency. Further, as described above, an IMD 14 may only perform the example method during daytime hours, or when patient is awake and not attempting to sleep, and/or only in response to an indication received from a patient 12 via patient programmer 20. Additionally, an IMD 14 need not update metric values 68, 70 each time a posture 62 or activity level 64 is determined. In some embodiments, for example, an IMD 14 may store postures 62 and activity levels 64 within memory 48, and may determine the metric values 68, 70 upon receiving a request for the values from one of programmers 20, 26.

Further, in some embodiments, as will be described in greater detail below, an IMD 14 does not determine the metric values 68, 70, but instead provides postures 62 and activity levels 64 to a computing device, such as clinician programmer 20 or patient programmer 26. In such embodiments, the computing device determines the metric values associated with each of the therapy parameter set/posture pair. Additionally, as described above, an IMD 14 need not determine postures 62 and activity levels 64, but may instead store samples of the signals generated by sensors 40. In such embodiments, the computing device may determine postures, activity levels, and metric values based on the samples.

Figure 6:
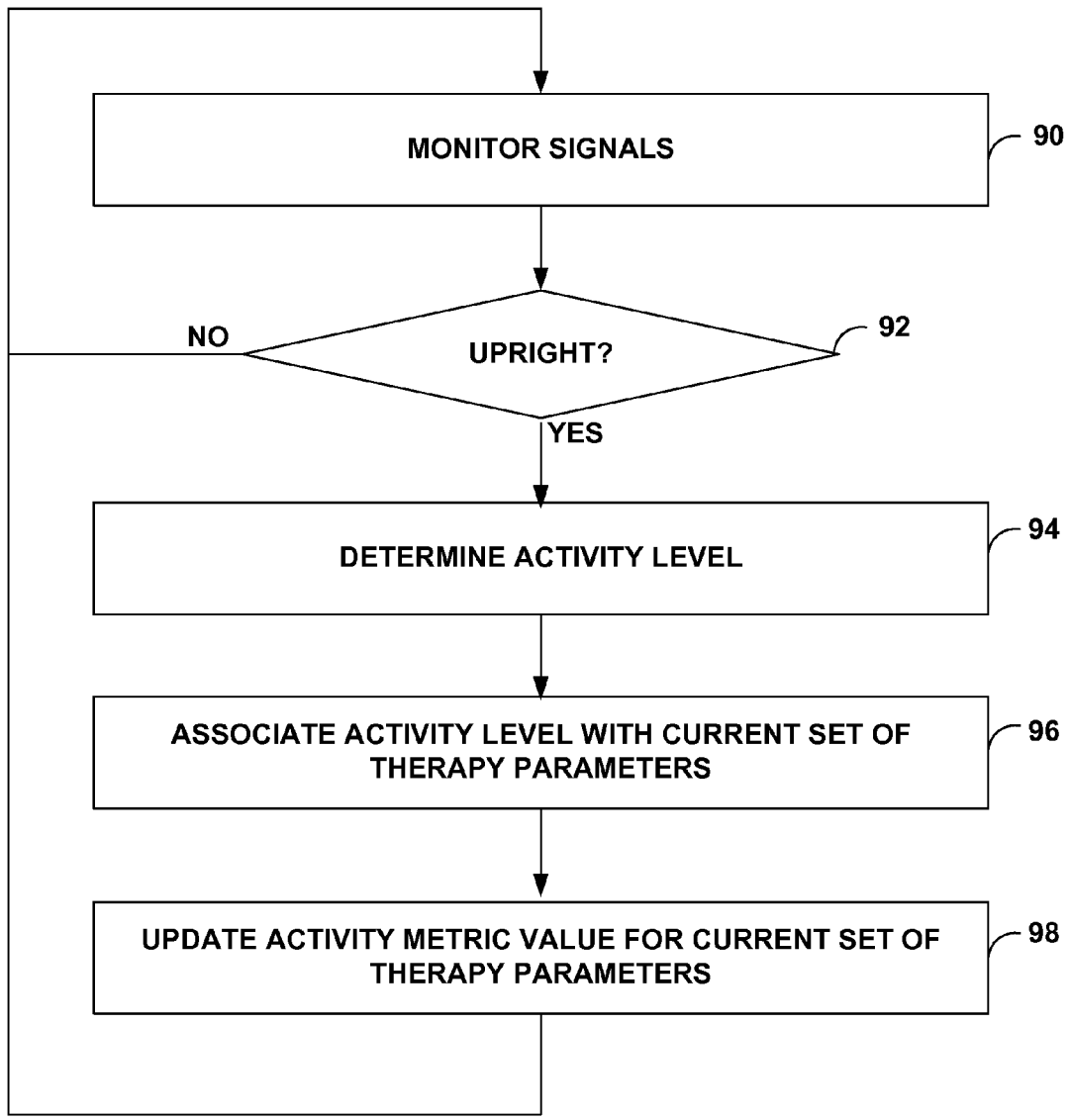
FIG. 6 is a flow diagram illustrating an example method for collecting activity information based on patient posture that may be employed by an implantable medical device.

FIG. 6 is a flow diagram illustrating an example method for collecting activity information based on patient posture that may be employed by an IMD 14. In some embodiments, an IMD 14 need not store postures 62, determine posture metrics 68, or associate activity levels 64 with particular postures. Rather, as illustrated in FIG. 6, an IMD 14 may limit activity information collection, e.g., determination of activity levels 64, to times when a patient 12 is in a target posture, e.g., a posture of interest. A target posture may be, for example, upright, e.g., standing or sitting, or may be only standing. In some cases, the activity of a patient 12 while in such target postures may be particularly indicative of the effectiveness of a therapy.

An IMD 14 monitors one or more signals generated by sensors 40 (90). For example, an IMD 14 may monitor signals generated by a plurality of orthogonally aligned accelerometers, as described above. Each of the accelerometers may be substantially aligned with a respective axis of the body of a patient 12.

An IMD 14 determines whether a patient 12 is upright based upon the signals (92). If patient a 12 is upright, IMD 14 determines an activity level 64 (94), and associates the determined activity level 64 with a current set of therapy parameters 60 (96). For example, an IMD 14 may determine a number of activity counts based on the one or more of the accelerometer signals, as described above, and may store the determined activity level 64 in memory 48 with an indication of the current therapy parameter set 60. An IMD 14 may then update one or more activity metric values 68 associated with the current therapy parameter set 60 (98).

As is the case with the example method illustrated in FIG. 5, an IMD 14 may periodically perform the example method illustrated in FIG. 6, e.g., may periodically monitor the signals generated by sensors 40 (90), determine whether a patient 12 is in a posture of interest (92), determine activity levels 64 when a patient 12 is in the posture of interest (94), and associate the determined activity levels 64 with a current therapy parameter set 60 (96). Further, as described above, an IMD 14 may only perform the example method during daytime hours, or when patient is awake and not attempting to sleep, and/or only in response to an indication received from a patient 12 via patient programmer 20. Additionally, an IMD 14 need not update activity metric values 70 each time an activity level 64 is determined. In some embodiments, for example, an IMD 14 may store activity levels 64 within memory, and may determine the activity metric values 70 upon receiving a request for the values from one of programmers 20, 26.

Further, in some embodiments, as will be described in greater detail below, an IMD 14 does not determine the activity metric values 70, but instead provides activity levels 64 to a computing device, such as clinician programmer 20 or patient programmer 26. In such embodiments, the computing device determines the activity metric values associated with each of the therapy parameter sets. Additionally, as described above, an IMD 14 need not determine postures 62 and activity levels 64, but may instead store samples of the signals generated by sensors 40. In such embodiments, the computing device may determine postures, activity levels, and activity metric values based on the samples.

Figure 7:
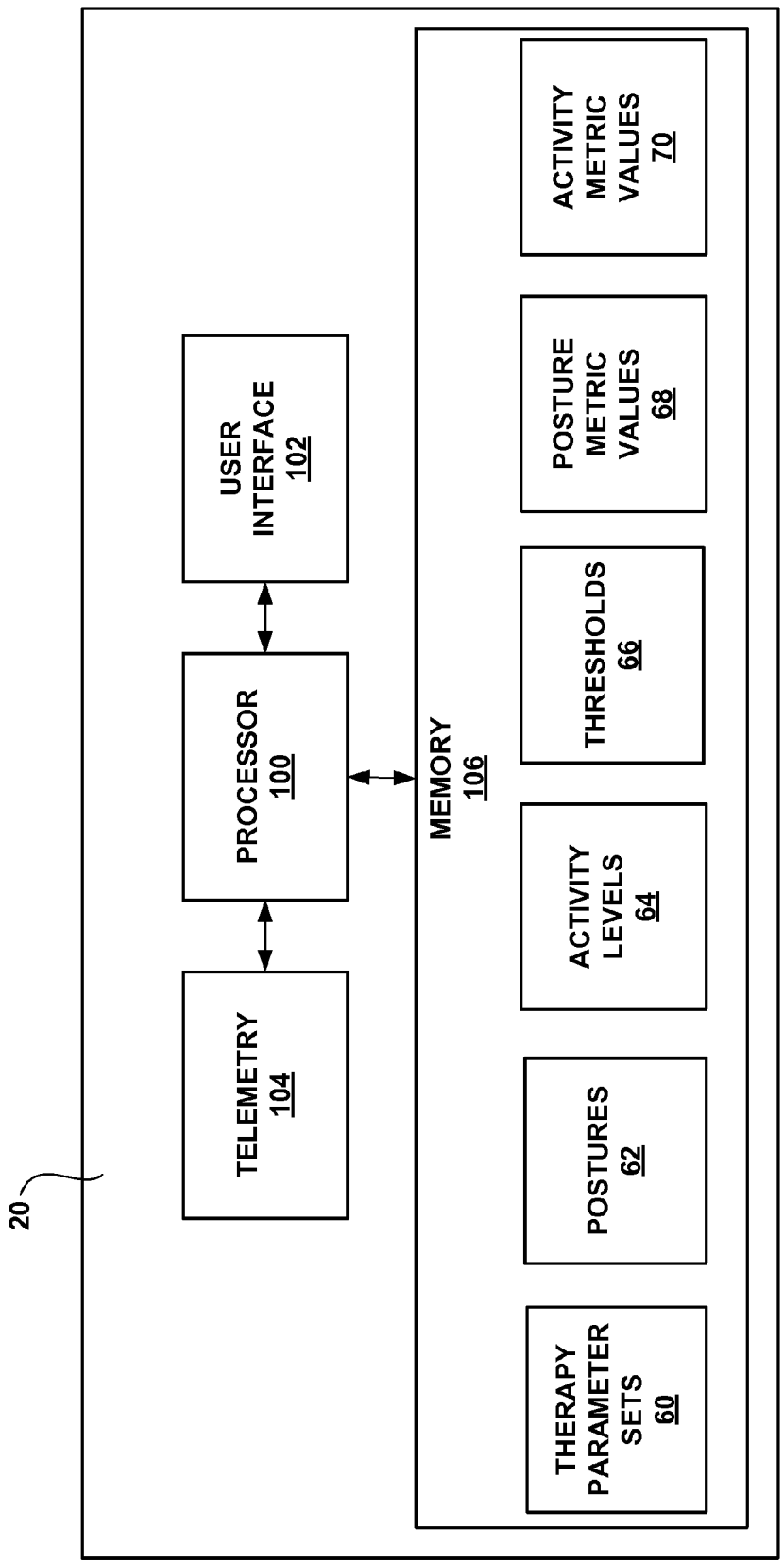
FIG. 7 is a block diagram illustrating an example clinician programmer.

FIG. 7 is a block diagram illustrating clinician programmer 20. A clinician may interact with a processor 100 via a user interface 102 in order to program therapy for a patient 12, e.g., specify therapy parameter sets. Processor 100 may provide the specified therapy parameter sets to an IMD 14 via telemetry circuit 104.

At another time, e.g., during a follow up visit, processor 100 may receive information identifying a plurality of therapy parameter sets 60 from an IMD 14 via telemetry circuit 104, which may be stored in a memory 106. The therapy parameter sets 60 may include the originally specified parameter sets, and parameter sets resulting from manipulation of one or more therapy parameters by a patient 12 using patient programmer 26. In some embodiments, processor 100 also receives posture and activity metric values 68, 70 associated with the therapy parameter sets 60, and stores the metric values in memory 106. In other embodiments, processor 100 may receive postures 62 and activity levels 64 associated with the therapy parameter sets 60, and determine values 68, 70 of one or more metrics for each of the plurality of therapy parameter sets 60 using any of the techniques described above with reference to an IMD 14 and FIGS. 2A, 2B and 4. In still other embodiments, processor 100 receives samples of signals generated by sensors 40, either from an IMD 14, from a separate monitor that includes or is coupled to sensors 40, or directly from sensors 40, and determines postures 62, activity levels 64 and metric values 68, 70 based on signals using any of the techniques described above with reference to the IMD 14 and FIGS. 2A, 2B and 4.

Upon receiving or determining posture and activity metric values 68, 70, processor 100 may generate a list of the therapy parameter sets 60 and associated metric values 68, 70, and present the list to the clinician. User interface 102 may include display 22, and processor 100 may display the list via display 22. The list of therapy parameter sets 60 may be ordered according to a metric value, and where a plurality of metric values are associated with each of the parameter sets, the list may be ordered according to the values of the metric selected by the clinician. Processor 100 may also present other posture or activity information to a user, such as a trend diagram of activity or posture over time, or a histogram, pie chart, or other illustration of percentages of time that a patient 12 was within certain postures 62, or activity levels 64 were within certain ranges. Processor 100 may generate such charts or diagrams using postures 62 and activity levels 64 associated with a particular one of the therapy parameter sets 60, or all of the postures 62 and activity levels 64 recorded by an IMD 14.

User interface 102 may include display 22 and keypad 24, and may also include a touch screen or peripheral pointing devices as described above. Processor 100 may include a microprocessor, a controller, a DSP, an ASIC, an FPGA, discrete logic circuitry, or the like. Memory 106 may include program instructions that, when executed by processor 100, cause clinician programmer 20 to perform the functions ascribed to clinician programmer 20 herein. Memory 106 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

FIG. 8 illustrates an example list 110 of therapy parameter sets 60 and associated metric values 68, 70 that may be presented by clinician programmer 20. Each row of example list 110 includes an identification of one of therapy parameter sets 60, the parameters of the therapy parameter set, and an identification of the postures assumed by a patient 12 when the parameter set was active, e.g., the categories of postures 62 associated with the parameter set. In the illustrated example, each of the listed therapy parameter sets 60 is associated with two postural categories, i.e., upright and recumbent.

Each of the listed therapy parameter sets is also associated with two values 70 for each of two activity metrics, i.e., an activity metric value 70 for each posture associated with the therapy parameter set. The activity metrics illustrated in FIG. 8 are a percentage of time active, and an average number of activity counts per hour. An IMD 14 or programmer 20 may determine the average number of activity counts per hour for one of the illustrated therapy parameter set/posture pairs by identifying the total number of activity counts associated with the parameter set and the posture, and the total amount of time that patient was in that posture while the IMD 14 was using the parameter set. An IMD 14 or programmer 20 may determine the percentage of time active for one of the illustrated therapy parameter set/posture pairs by comparing each activity level associated with the parameter set and posture to an "active" threshold, and determining the percentage of activity levels above the threshold. As illustrated in FIG. 8, an IMD 14 or programmer 20 may also compare each activity level for the therapy parameter/posture pair set to an additional, "high activity" threshold, and determine a percentage of activity levels above that threshold.

As illustrated in FIG. 8, list 110 may also include a posture metric 68. In the illustrated example, list 110 includes as posture metrics 68 for each therapy parameter set the percentage of time that patient 12 was in each posture when the therapy parameter set was active. Programmer 20 may order list 110 according to a user-selected one of the metrics 68, 70.

Figure 9:
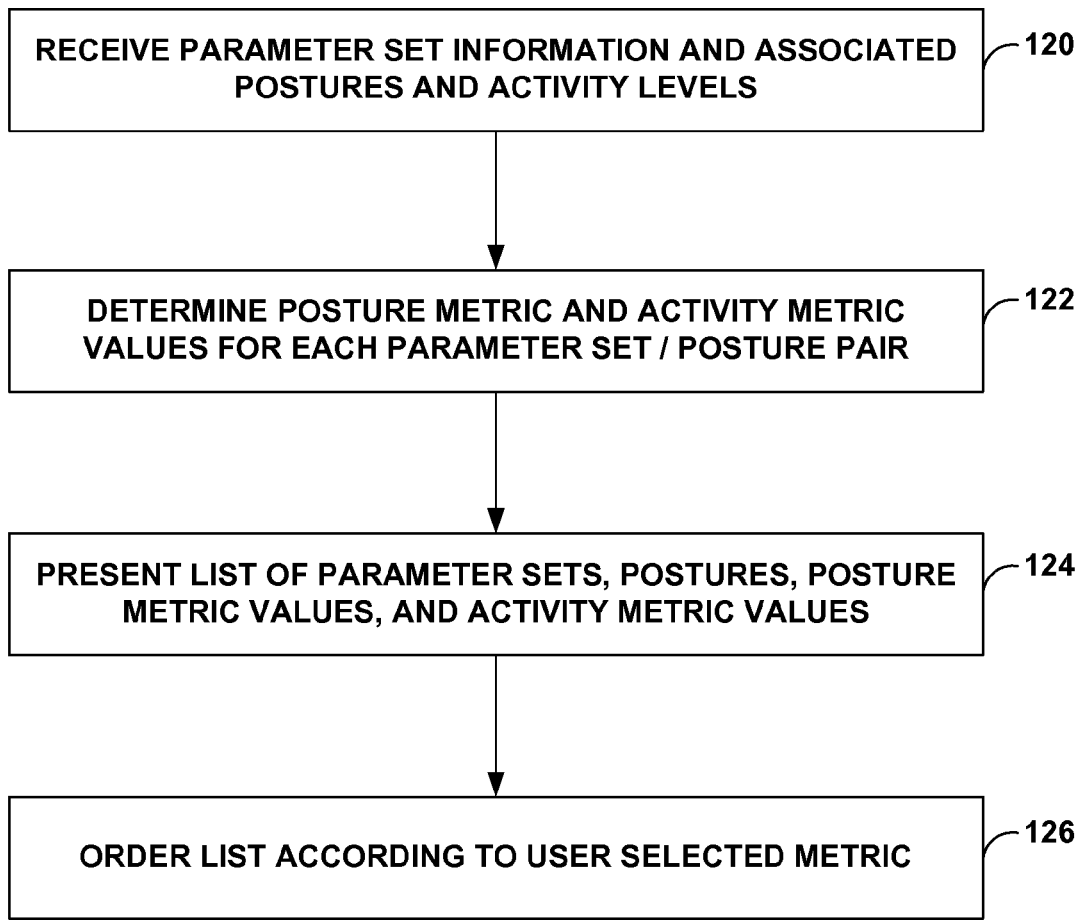
FIG. 9 is a flow diagram illustrating an example method for displaying a list of therapy parameter sets and associated posture and activity metric values that may be employed by a clinician programmer.

FIG. 9 is a flow diagram illustrating an example method for displaying a list of therapy parameter sets 60 and associated metric values 68, 70 that may be employed by a clinician programmer 20. Although described with reference to clinician programmer 20, patient programmer 26 or another computing device may perform the method illustrated by FIG. 7.

Programmer 20 receives information identifying therapy parameter sets 60 and associated postures 62 and activity levels 64 from an IMD 14 (120). Programmer 20 then determines one or more posture and activity metric values 68, 70 for each of the therapy parameter sets based on the postures 62 and activity levels 64 associated with the therapy parameter sets (122). In other embodiments, an IMD 14 determines the metric values, and provides them to programmer 20, or provides samples of signals associated with therapy parameter sets to programmer 20 for determination of metric values, as described above. After receiving or determining metric values 68, 70, programmer 20 presents a list 110 of therapy parameter sets 60 and associated metric values 68, 70 to the clinician, e.g., via display 22 (124). Programmer 20 may order list 110 of therapy parameter sets 60 according to the associated metric values, and the clinician may select according to which of a plurality of metrics list 110 is ordered via a user interface 82 (126).

In some embodiments, as discussed above, one or more of an IMD 14, programmers 20, 26, or another computing device may conduct a sensitivity analysis of one or more posture and/or activity metric values 68, 70 to identify one or more therapy parameter sets for use in delivering therapy to a patient 12. The sensitivity analysis may be performed as an alternative or in addition to presenting posture and activity information to a user for evaluation of therapy parameter sets.

The IMD, programmer, or the other computing device may perform the sensitivity analysis to identify a value for each therapy parameters that defines substantially maximum or minimum posture and/or activity metric values. In other words, the sensitivity analysis identifies therapy parameter values that yield the "best" metric values. The IMD, programmer, or other computing device then identifies one or more baseline therapy parameter sets that include the identified parameter values, and stores the baseline therapy parameter sets as therapy parameter sets 60 or separately within memory 48 of an IMD 14. An IMD 14 may then deliver stimulation according to the baseline therapy parameter sets. The baseline therapy parameter sets include the values for respective therapy parameters that produced the best activity and/or posture metric values.

In some embodiments, the IMD, programmer, or other computing device may adjust the therapy delivered by an IMD 14 based on a change in the activity or posture metric values 68, 70. In particular, the IMD, programmer, or other computing device may perturb one or more therapy parameters of a baseline therapy parameter set, such as pulse amplitude, pulse width, pulse rate, duty cycle, and duration, to determine if the current posture and/or activity metric values improve or worsen during perturbation. In some embodiments, values of the therapy parameters may be iteratively and incrementally increased or decreased until substantially maximum or minimum values of the posture and/or activity metric are again identified.

Figure 10:
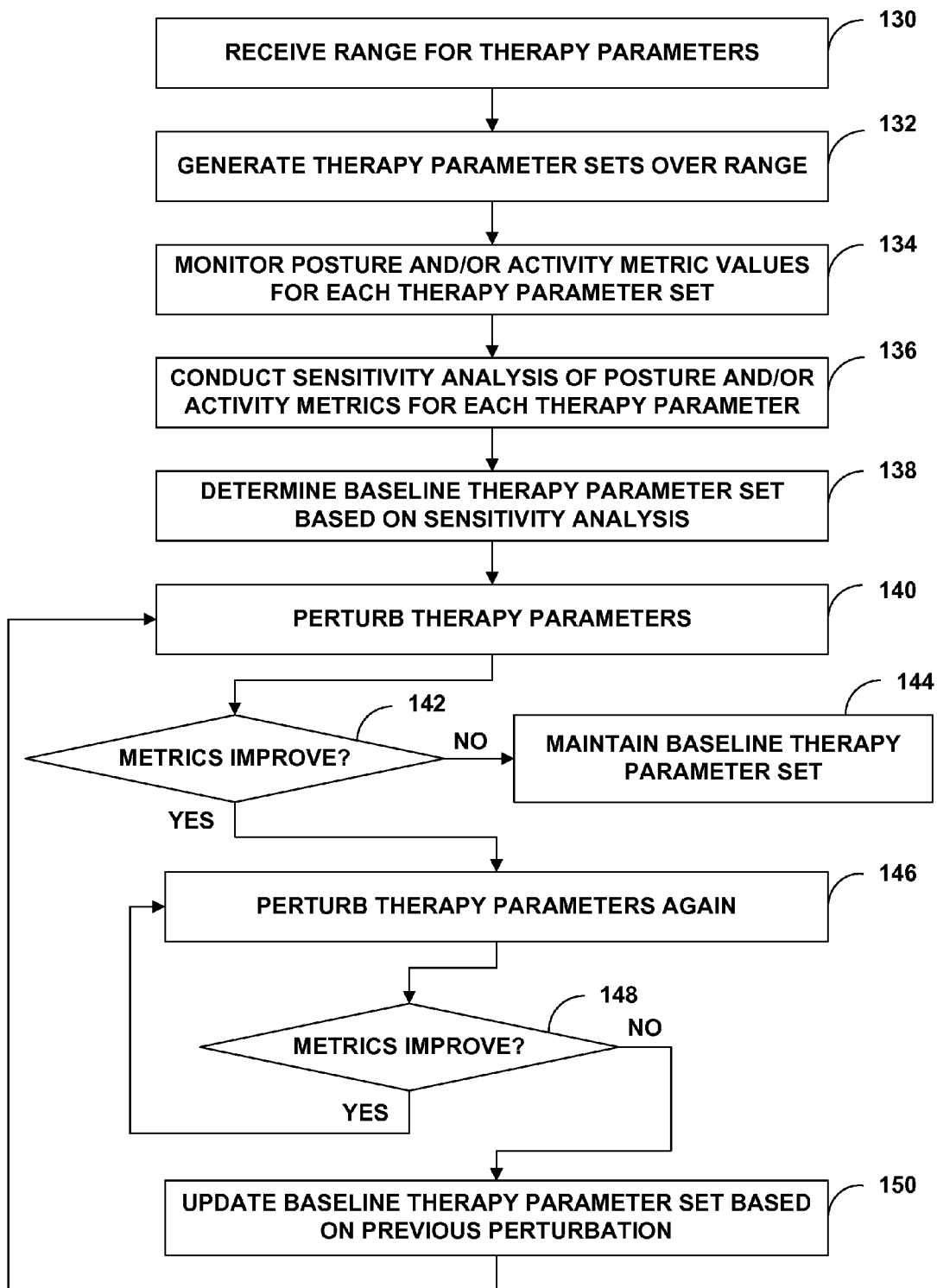
FIG. 10 is a flow diagram illustrating an example method for identifying a therapy parameter set based on collected posture and/or activity information that may be employed by a medical device.

FIG. 10 is a flow diagram illustrating an example method for identifying a therapy parameter set, e.g., a baseline therapy parameter set, based on collected posture and/or activity information that may be employed by an IMD 14. For ease of description, a number of the actions that are part of the method illustrated in FIG. 10 are described as being performed by an IMD 14. However, in some embodiments, as discussed above, an external computing device, such as one of programmers 20, 26, and more particularly the processor of such a computing device, may perform one or more of the activities attributed to an IMD 14 below.

An IMD 14 receives a therapy parameter range for therapy parameters (130) from a clinician using clinician programmer 20 via telemetry circuit 50. The range may include minimum and maximum values for each of one or more individual therapy parameters, such as pulse amplitude, pulse width, pulse rate, duty cycle, duration, dosage, infusion rate, electrode placement, and electrode selection. The range may be stored in memory 48, as described in reference to FIG. 4.

Processor 46 then randomly or non-randomly generates a plurality of therapy parameter sets 60 with individual parameter values selected from the range (132). The generated therapy parameter sets 60 may substantially cover the range, but do not necessarily include each and every therapy parameter value within the therapy parameter range, or every possible combination of therapy parameters within the range. The generated therapy parameter sets 60 may also be stored in memory 48.

An IMD 14 monitors at least one posture or activity metric 68, 70 of a patient 12 for each of the randomly or non-randomly generated therapy parameter sets 60 spanning the range (134). The values of the metrics corresponding to each of the therapy parameter sets 60 may be stored in memory 48 of an IMD 14, as described above. An IMD 14 then conducts a sensitivity analysis of the one or more posture and/or activity metrics for each of the therapy parameters, e.g., each of pulse amplitude, pulse width, pulse rate and electrode configuration (136). The sensitivity analysis determines a value for each of the therapy parameters that produced a substantially maximum or minimum value of the one or more metrics. One or more baseline therapy parameter sets are then determined based on the therapy parameter values identified by the sensitivity analysis (138). The baseline therapy parameter sets include combinations of the therapy parameter values individually observed to produce substantially maximum or minimum values of the one or more posture or activity metrics 68, 70. The baseline therapy parameter sets may also be stored with therapy parameters sets 60 in memory 48. In some embodiments, the baseline therapy parameter sets may be stored separately from the generated therapy parameter sets.

After this initial baseline therapy parameter set identification phase of the example method, an IMD 14 may control delivery of the therapy based on the baseline therapy parameter sets. Periodically during the therapy, an IMD 14 checks to ensure that the baseline therapy parameter sets continues to define substantially maximum or minimum posture and/or activity metric values for a patient 12. An IMD 14 first perturbs at least one of the therapy parameter values of a baseline therapy parameter set (140). The perturbation comprises incrementally increasing and/or decreasing the therapy parameter value, or changing electrode polarities. A perturbation period may be preset to occur at a specific time, in response to a physiological parameter monitored by the IMD, or in response to a signal from the patient or clinician. The perturbation may be applied for a single selected parameter or two or more parameters, or all parameters in the baseline therapy parameter set. Hence, numerous parameters may be perturbed in sequence. For example, upon perturbing a first parameter and identifying a value that produces a maximum or minimum metric value, a second parameter may be perturbed with the first parameter value fixed at the identified value. This process may continue for each of the parameters in a baseline therapy parameter set, and for each of a plurality of baseline therapy parameter sets.

Upon perturbing a parameter value, an IMD 14 then compares a value of the one or more metrics defined by the perturbed therapy parameter set to a corresponding value of the metric defined by the baseline therapy parameter set during the initial baseline identification phase (142). If the metric values do not improve with the perturbation, an IMD 14 maintains the unperturbed baseline therapy parameter set values (144). If the metric values do improve with the perturbation, an IMD 14 perturbs the therapy parameter value again (146) in the same direction that defined the previous improvement in the metric values. An IMD 14 compares a value of the metrics defined by the currently perturbed therapy parameter set to the metric values defined by the therapy parameter set of the previous perturbation (148). If the metric values do not improve, an IMD 14 updates the baseline therapy parameter set based on the therapy parameter values from the previous perturbation (150). If the metric values improve again, an IMD 14 continues to perturb the therapy parameter value (146).

Periodically checking the values of one or more metrics for the baseline therapy parameter set during this perturbation phase of the example method allows an IMD 14 to consistently deliver a therapy to a patient 12 that defines a substantially maximum or minimum posture and/or activity metric values 68, 70. This may allow the patient's symptoms to be continually managed even as the patient's physiological parameters and symptoms change.

Various embodiments of the invention have been described. However, one skilled in the art will recognize that various modifications may be made to the described embodiments without departing from the scope of the invention. For example, the invention may be embodied as a computer-readable medium that includes instructions to cause a processor to perform any of the methods described herein.

As another example, although described herein primarily in the context of treatment with an implantable neurostimulator, the invention is not so limited. The invention may be embodied in any implantable medical device that delivers a therapy, such as a cardiac pacemaker or an implantable pump. Further, the invention may be implemented via an external, e.g., non-implantable, medical device. In such embodiments, the external medical device itself may include a user interface and display to present activity information to a user, such as a clinician or patient, for evaluation of therapy parameter sets.

As discussed above, the overall activity level of a patient, e.g., the extent to which the patient is on his or her feet and moving or otherwise active, rather than sitting or lying in place, may be negatively impacted by any of a variety of ailments or symptoms. Accordingly, the activity level, postures and posture change frequency of a patient may reflect the progression, status, or severity of the ailment or symptom. Further, the extent that a patient is active and upright may reflect the efficacy of a particular therapy or therapy parameter set in treating the ailment or symptom. In other words, it may generally be the case that the more efficacious a therapy or therapy parameter set is, the more active and upright a patient will be.

As discussed above, in accordance with the invention, activity and posture metrics may be monitored, and used to evaluate the status, progression or severity of an ailment or symptom, or the efficacy of therapies or therapy parameter sets used to treat the ailment or symptom. As an example, chronic pain chronic pain may cause a patient to avoid particular activities, high levels of activity, or activity in general. Systems according to the invention may monitor activity and activity metrics to evaluate the extent to which the patient is experiencing pain.

In some embodiments, systems according to the invention may include any of a variety of medical devices that deliver any of a variety of therapies to treat chronic pain, such as SCS, DBS, cranial nerve stimulation, peripheral nerve stimulation, or one or more drugs. Systems may use the techniques of the invention described above to determine activity and posture metrics for the patient and evaluate such therapies, e.g., by associating values for the metric with therapy parameter sets for delivery of such therapies. Systems according to the invention may thereby evaluate the extent to which a therapy or therapy parameter set is alleviating chronic pain by evaluating the extent to which the therapy or therapy parameter set allows the patient to be more active or engage in particular activities or postures.

As another example, psychological disorders may cause a patient to be less active and more recumbent. Accordingly, embodiments of the invention may determine activity and posture metrics to track the status or progression of a psychological disorder, such as depression, mania, bipolar disorder, or obsessive-compulsive disorder. Further, systems according to the invention may include any of a variety of medical devices that deliver any of a variety of therapies to treat a psychological disorder, such as DBS, cranial nerve stimulation, peripheral nerve stimulation, vagal nerve stimulation, or one or more drugs. Systems may use the techniques of the invention described above to associate activity and posture metric values with the therapies or therapy parameter sets for delivery of such therapies, and thereby evaluate the extent to which a therapy or therapy parameter set is alleviating the psychological disorder by evaluating the extent to which the therapy parameter set improves the overall activity level of the patient, as indicated by activity and posture.

Movement disorders, such as tremor, Parkinson's disease, multiple sclerosis, epilepsy, and spasticity may also affect the overall activity level of a patient, as well as posture. Further, movement disorders are also characterized by irregular, uncontrolled and generally inappropriate movements, e.g., tremor or shaking, particularly of the limbs. In addition to using the sensors described above to sense the overall activity level of a movement disorder patient, some embodiments of the invention may use such sensors to detect the types of inappropriate movements associated with the movement disorder. For example, accelerometers, piezoelectric crystals, or EMG electrodes located in the trunk or limbs of a patient may be able to detect inappropriate movements such as tremor or shaking Movement disorders and psychological disorders are examples of neurological disorders that may be treated according to the therapy and therapy evaluation described herein.

Systems according to the invention may periodically determine the level or severity of such movements based on the signals output by such sensors, associate the inappropriate movement levels with current therapy parameter sets, and determine activity metric values for therapy parameter sets based on the associated levels. For example, a processor of such a system may determine a frequency or amount of time that such movements exceeded a threshold during delivery of a therapy parameter set as an inappropriate movement based activity metric value for the therapy parameter set.

Another activity-related movement disorder symptom that is relatively specific to Parkinson's disease is "gait freeze." Gait freeze may occur when a Parkinson's patient is walking Gait freeze refers to a relatively sudden inability of a Parkinson's patient to take further steps. Gait freeze is believed to result from a neurological failure and, more specifically, a failure in the neurological signaling from the brain to the legs.

In some embodiments, in addition to the activity metrics described above, any of the devices or processors described above may additionally identify gait freeze events based on the signals output by sensors 40. For example, processor 46, or another processor of the system, may detect a relatively sudden cessation of activity associated with a gait event based on the output of accelerometers, piezoelectric crystals, EMG electrodes, or other sensors that output signals based on footfalls or impacts associated with, for example, walking When experiencing a gait freeze event, a patient may "rock" or "wobble" while standing in place, as if attempting unsuccessfully to move. In some embodiments, processor 46 may monitor any of sensors 40 that output signals as a function of posture discussed above, such as a 3-axis accelerometer, to detect the minor, rhythmic changes in posture associated with rocking or wobbling. Processor 46 may detect a gait freeze event as when it occurs based on one or more of the posture or activity sensors. For example, processor 46 may confirm that a relatively sudden cessation of activity is in fact a gait freeze event based on rocking or wobbling indicated by posture sensors.

In some embodiments, the processor may detect a gait freeze prior to onset. For example, sensors 40 may include EMG or EEG electrodes, and processor 46 may detect a gait freeze prior to onset based on irregular EMG or EEG activity. EMG signals, as an example, demonstrate irregularity just prior to a freezing episode, and a processor may detect this irregularity as being different from the EMG signals typically associated with walking In other words, a walking patient may exhibit normal EMG pattern in the legs, which may be contrasted with EMG activity and timing changes that precede freezing.

In general, EMG signals from right and left leg muscles include a regularly alternating rhythm pattern that characterizes normal gait. When the "timing" of the pattern fails, there is no longer a regular rhythm, and a gait freeze may result. Accordingly, a processor may detect irregularity, variability, or asymmetry, e.g., within and between right and left leg muscles, in one or more EMG signals, and may detect an oncoming gait freeze prior to occurrence based on the detection. In some embodiments, the processor may compare the EMG signals to one or more thresholds to detect gait freeze. Comparison to a threshold may, for example, indicate an absolute value or increase in irregularity, variability, asymmetry that exceeds a threshold, indicating an oncoming gait freeze. In some embodiments, thresholds may be determined based on EMG signal measurements made when the patient is walking normally.

Whether or not gait freeze is detected prior to r during occurrence, the processor may associate the occurrence of the gait freeze event with a current therapy parameter set used to control delivery of a therapy for Parkinson's disease, such as DBS or a drug. Additionally, the processor may determine or update an activity metric value for the therapy parameter set based on the gait freeze event, such as a total number of gait freeze events for the therapy parameter set, or an average number of gait freeze events over a period of time.

Systems according to the invention may include any of a variety of medical devices that deliver any of a variety of therapies to treat movement disorders, such as DBS, cortical stimulation, or one or more drugs. Baclofen, which may or may not be intrathecally delivered, is an example of a drug that may be delivered to treat movement disorders. Systems may use the techniques of the invention described above to associate any of the above-described sleep quality or activity metrics with therapies or therapy parameter sets for delivery of such therapies. In this manner, such systems may allow a user to evaluate the extent to which a therapy or therapy parameter set is alleviating the movement disorder by evaluating the extent to which the therapy parameter set improves the sleep quality, general activity level, inappropriate activity level, or number of gait freezes experienced by the patient.

Further, many of the ailments and symptoms described above, including movement disorders and chronic pain, may more generally affect the gait of a patient. More particularly, such symptoms and ailments may result in, as examples, an arrhythmic, asymmetric (left leg versus right leg), or unusually variable gait, or a gait with relative short stride lengths. Systems according to the invention may use sensors discussed above that output signals as a function of activity, and particularly as a function of footfalls or impacts, to monitor gait.

For example, a processor of such a system may periodically determine a value for asymmetry, variability, or stride length of gait, and associated such values with a current therapy parameter set used deliver any of the therapies discussed herein with reference to chronic pain or movement disorders. The processor may determine an activity metric value based on gait by, for example, averaging the gait values associated with a therapy parameter set over a period of time, such as a day, week or month. The processor of the system that performs the techniques of the invention, such as gait monitoring and activity metric determination, may include one or more of a processor of an IMD or a processor of a programming or computing device, as discussed above.

Additionally, the invention is not limited to embodiments in which a programming device receives information from the medical device, or presents information to a user. Other computing devices, such as handheld computers, desktop computers, workstations, or servers may receive information from the medical device and present information to a user as described herein with reference to programmers 20, 26. A computing device, such as a server, may receive information from the medical device and present information to a user via a network, such as a local area network (LAN), wide area network (WAN), or the Internet. Further, in some embodiments, the medical device is an external medical device, and may itself include user interface and display to present activity information to a user, such as a clinician or patient, for evaluation of therapy parameter sets.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Posture and activity metric values collected during use of the trial neurostimulator or pump may be used by a clinician to evaluate the prospective therapy parameter sets, and select parameter sets for use by the later implanted non-trial neurostimulator or pump. The posture and activity metric values may be collected by the trial device in the manner described above with reference to an IMD 14, or by a programmer 20, 26 or other computing device, as described above. After a trial period, a programmer or computing device may present a list of prospective parameter sets and associated metric values to a clinician. The clinician may use the list to identify potentially efficacious parameter sets, and may program a permanent implantable neurostimulator or pump for the patient with the identified parameter sets.

In some embodiments, a trial neurostimulator or pump, or a programmer or other external computing device, may perform a sensitivity analysis as described above on a range of therapy parameters tested by the trial neurostimulator or pump during a trialing period. A permanent implantable neurostimulator or pump may be programmed with the one or more baseline therapy parameter sets identified by the sensitivity analysis, and may periodically perturb the baseline therapy parameter sets to maintain effective therapy in the manner described above.

Additionally, as discussed above, the invention is not limited to embodiments in which the therapy delivering medical device monitors activity or posture. In some embodiments, a separate monitoring device monitors values of one or more physiological parameters of the patient instead of, or in addition to, a therapy delivering medical device. The monitor may include a processor 46 and memory 48, and may be coupled to or include sensors 40, as illustrated above with reference to an IMD 14 and FIGS. 2A, 2B, and 4.

The monitor may identify postures and activity levels based on the values of the monitored physiological parameter values, and determine posture and activity metric values based on the identified postures and activity levels as described herein with reference to an IMD 14. Alternatively, the monitor may transmit indications of posture and activity levels to an IMD, programmer, or other computing device, which may then determine posture and activity metric values. As another alternative, the monitor may transmit recorded physiological parameter values to an IMD, programmer, or other computing device for determination of postures, activity levels, and/or posture and activity metric values.

Figure 11:
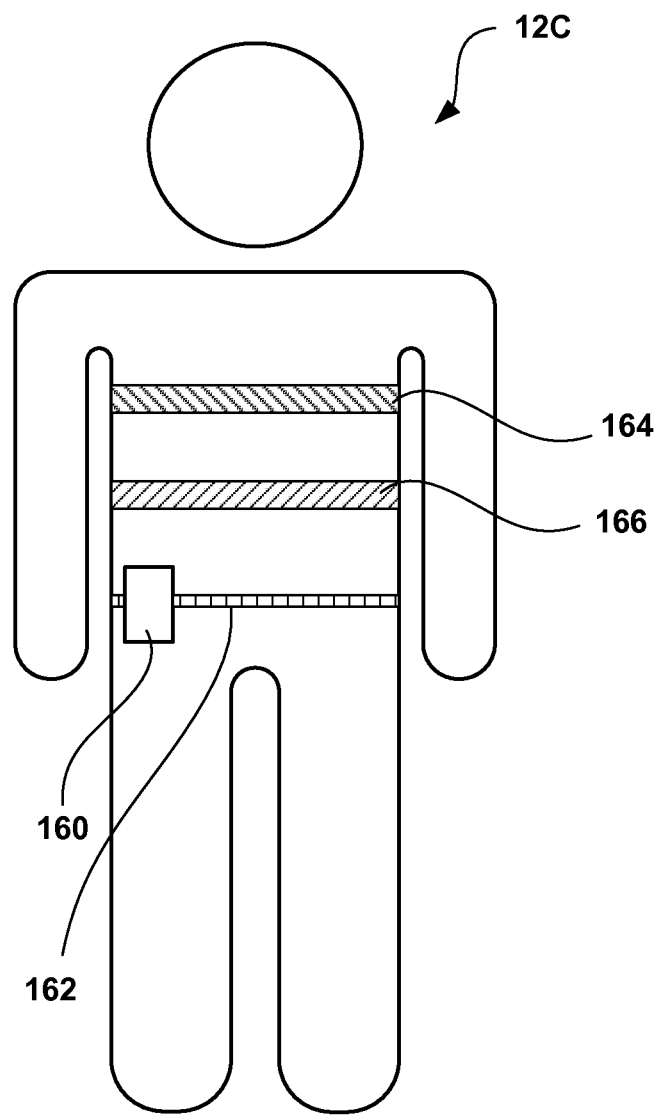
FIG. 11 is a conceptual diagram illustrating a monitor that monitors values of one or more physiological parameters of the patient.

FIG. 11 is a conceptual diagram illustrating a monitor 160 that monitors the posture and activity of the patient instead of, or in addition to, a therapy delivering medical device. In the illustrated example, monitor 160 is configured to be attached to or otherwise carried by a belt 162, and may thereby be worn by patient 12C. FIG. 11 also illustrates various sensors 40 that may be coupled to monitor 160 by leads, wires, cables, or wireless connections.

In the illustrated example, patient 12C wears an ECG belt 164. ECG belt 164 incorporates a plurality of electrodes for sensing the electrical activity of the heart of patient 12C. The heart rate and, in some embodiments, ECG morphology of patient 12C may monitored by monitor 150 based on the signal provided by ECG belt 164. Examples of suitable belts 164 for sensing the heart rate of patient 12C are the "M" and "F" heart rate monitor models commercially available from Polar Electro. In some embodiments, instead of belt 160, patient 12C may wear a plurality of ECG electrodes attached, e.g., via adhesive patches, at various locations on the chest of the patient, as is known in the art. An ECG signal derived from the signals sensed by such an array of electrodes may enable both heart rate and ECG morphology monitoring, as is known in the art. Signals received from EEG electrodes 174A-C may be analyzed to determine sleep states, e.g., using techniques and circuitry described with reference to FIG. 3.

As shown in FIG. 11, patient 12C may also wear a respiration belt 166 that outputs a signal that varies as a function of respiration of the patient. Respiration belt 166 may be a plethysmograpy belt, and the signal output by respiration belt 166 may vary as a function of the changes is the thoracic or abdominal circumference of patient 12C that accompany breathing by the patient. An example of a suitable belt 166 is the TSD201 Respiratory Effort Transducer commercially available from Biopac Systems, Inc. Alternatively, respiration belt 166 may incorporate or be replaced by a plurality of electrodes that direct an electrical signal through the thorax of the patient, and circuitry to sense the impedance of the thorax, which varies as a function of respiration of the patient, based on the signal. In some embodiments, ECG and respiration belts 164 and 166 may be a common belt worn by patient 12C, and the relative locations of belts 164 and 166 depicted in FIG. 11 are merely exemplary.

Monitor 160 may additionally or alternatively include or be coupled to any of the variety of sensors 40 described above with reference to FIGS. 2A, 2B, and 4, which output signals that vary as a function of activity level or posture. For example, monitor 160 may include or be coupled to a plurality of orthogonally aligned accelerometers, as described above.

Figure 12:
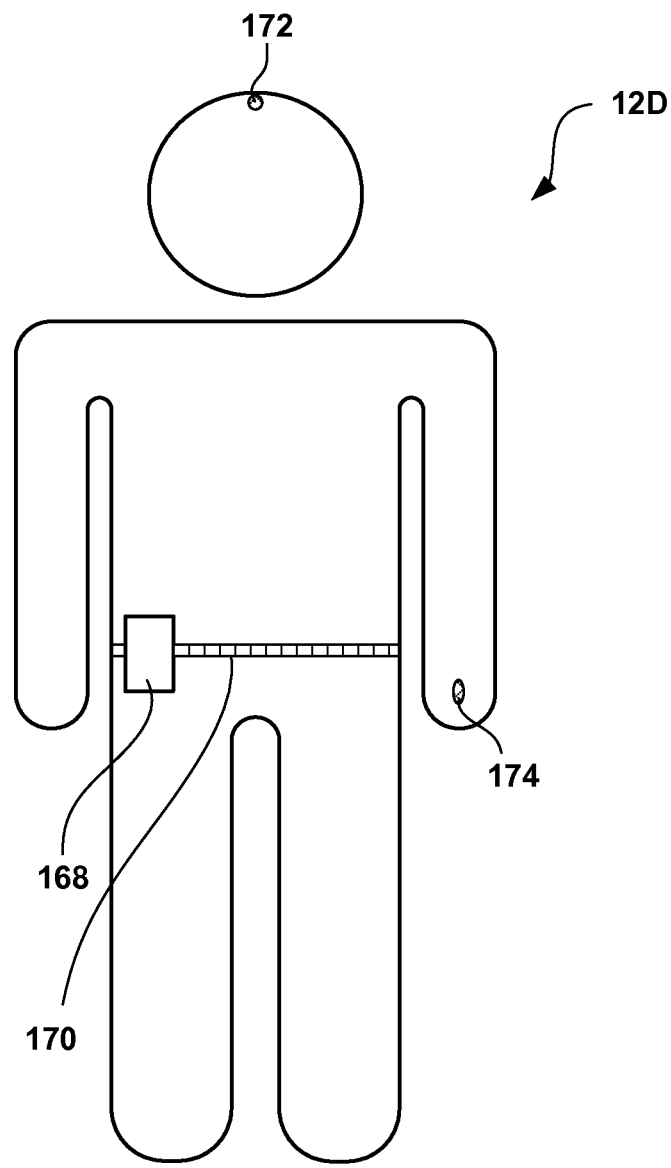
FIG. 12 is a conceptual diagram illustrating a monitor that monitors signals generated by one or more accelerometers disposed on the patient.

FIG. 12 is a conceptual diagram illustrating a monitor that monitors signals generated by one or more accelerometers instead of, or in addition to, such monitoring of signals generated by accelerometers or other sensors by a therapy delivering medical device. As shown in FIG. 12, patient 12D is wearing monitor 168 attached to belt 170. Monitor 168 is capable of receiving measurements from one or more sensors located on or within patient 12D. In the example of FIG. 12, accelerometers 172 and 174 are attached to the head and hand of patient 12, respectively. Accelerometers 172 and 174 may measure movement of the extremities, or activity level, of patient 12 to indicate when the patient moves during sleep or at other times during the day. Alternatively, more or less accelerometers or other sensors may be used with monitor 168.

Accelerometers 172 and 174 may be preferably multi-axis accelerometers, but single-axis accelerometers may be used. As patient 12D moves, accelerometers 172 and 174 detect this movement and send the signals to monitor 168. High frequency movements of patient 12D may be indicative of tremor, Parkinson's disease, or an epileptic seizure. Accelerometers 172 and 174 may be worn externally, i.e., on a piece or clothing or a watch, or implanted at specific locations within patient 12D. In addition, accelerometers 172 and 174 may transmit signals to monitor 168 via a wireless or a wired connection.

Monitor 168 may store the measurements from accelerometers 172 and 174 in a memory. In some examples, monitor 168 may transmit the measurements from accelerometers 172 and 174 directly to another device, such as an IMD 14 or a programmer. In this case, an the IMD 14 or programmer may analyze the measurements from accelerometers 172 and 174 to detect efficacy of therapy, control the delivery of therapy, detect sleep or monitor sleep quality using any of the techniques described herein.

In some examples, a rolling window of time may be used when analyzing measurements from accelerometers 172 and 174. Absolute values determined by accelerometers 172 and 174 may drift with time or the magnitude and frequency of patient 12D movement may not be determined by a preset threshold. For this reason, it may be advantageous to normalize and analyze measurements from accelerometers 172 and 174 over a discrete window of time. For example, the rolling window may be useful in detecting epileptic seizures. If monitor 168 or an IMD 14 detects at least a predetermined number of movements over a 15 second window, an epileptic seizure may be most likely occurring. In this manner, a few quick movements from patient 12 not associated with a seizure may not trigger a response, such as recording an incident in a memory or a change in therapy.

Figure 13:
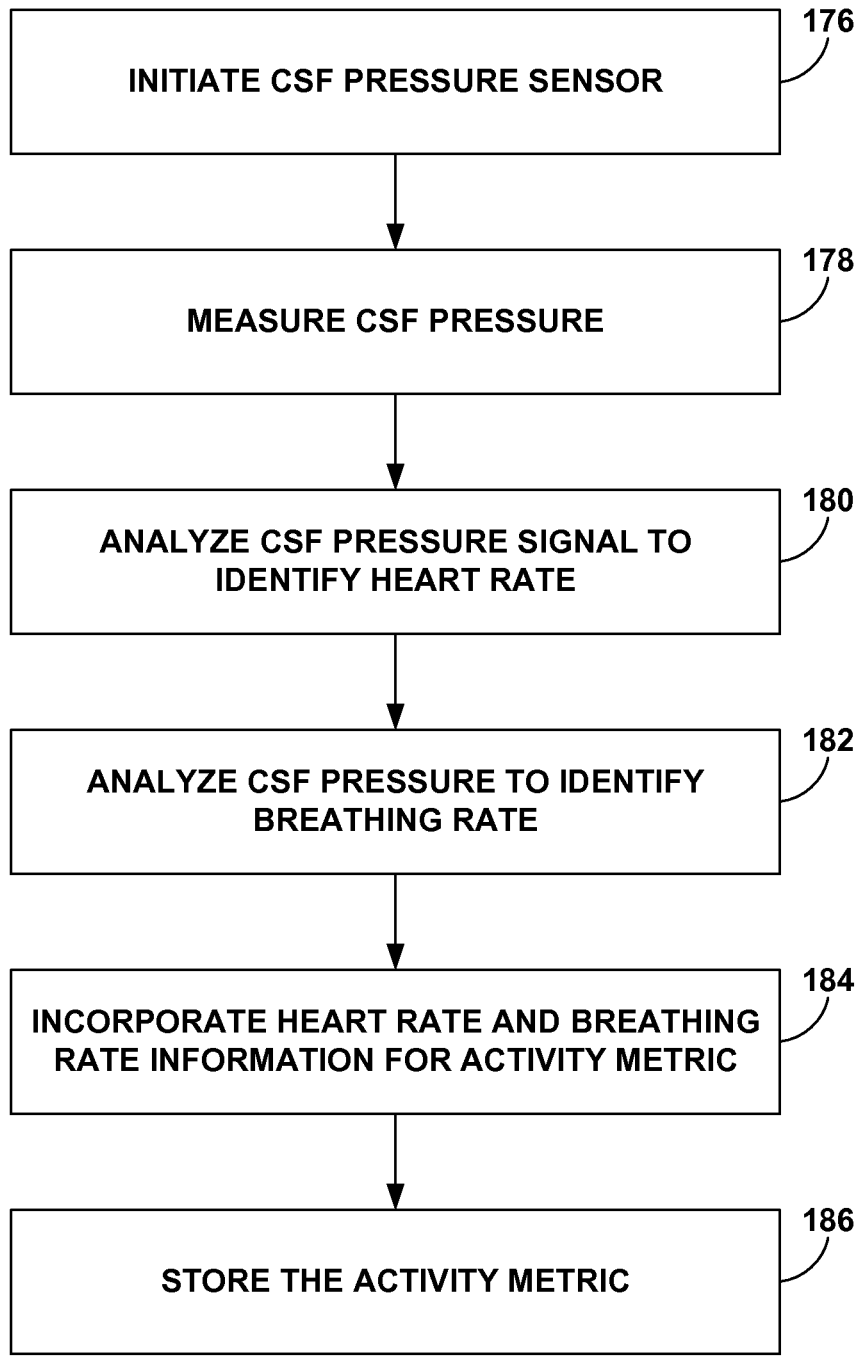
FIG. 13 is a flow diagram illustrating an example technique for monitoring the heart rate and breathing rate of a patient by measuring cerebral spinal fluid pressure.

FIG. 13 is a flow diagram illustrating monitoring the heart rate and breathing rate of a patient by measuring cerebral spinal fluid pressure. As discussed above, a physiological parameter that may be measured in a patient 12 is heart rate and respiration, or breathing, rate. In the example of FIG. 13, cerebral spinal fluid (CSF) pressure may be analyzed to monitor the heart rate and breathing rate of a patient 12. A clinician initiates a CSF pressure sensor for monitoring heart rate and/or breathing rate (176). Alternatively, the CSF pressure sensor may be implanted within the brain or spinal cord of a patient 12 to acquire accurate pressure signals. The CSF pressure sensor may transfer pressure data to an implanted or external device. As an example used herein, the CSF pressure sensor transmits signal data to an IMD 14.

Once the CSF pressure sensor is initiated, the CSF pressure sensor measures CSF pressure and transmits the data to an IMD 14 (178). An IMD 14 analyzes the CSF pressure signal to identify the heart rate (180) and breathing rate (182) of a patient 12. The heart rate and breathing rate can be identified within the overall CSF pressure signal. Higher frequency fluctuations (e.g. 40 to 150 beats per minute) can be identified as the heart rate while lower frequency fluctuations (e.g. 3 to 20 breaths per minute) in CSF pressure are the breathing rate. An IMD 14 may employ filters, transformations, or other signal processing techniques to identify the heart rate and breathing rate from the CSF pressure signal.

An IMD 14 may utilize the heart rate and breathing rate information when determining the activity level of a patient 12, as described above (184). For example, faster heart rates and faster breathing rates may indicate that the activity level of a patient 12 is higher than normal resting rates. An IMD 14 may then store values of an activity metric, provide the activity metric values to a programmer or other computing device, or use them to adjust stimulation therapy (186). As discussed above, CSF pressure may additionally be used to detect posture, and thereby determine posture metrics.

These and other embodiments are within the scope of the following claims.

The invention claimed is:

1. A method for evaluating a neurostimulation therapy delivered to a patient by an implantable medical device system, the method comprising:
   monitoring a plurality of signals, each of the signals generated by at least one sensor of the implantable medical device system as a function of at least one of activity or posture of the patient;
   determining whether the patient is in a target posture based on at least one of the signals;
   periodically determining an activity level of the patient based on at least one of the signals when the patient is in the target posture;
   periodically determining values of at least one activity metric based on the activity levels determined when the patient was in the target posture; and
   displaying for a user the determined activity metric values in a manner that is indicative of efficacy of the neurostimulation therapy delivered to the patient.

2. The method of claim 1, wherein the target posture is upright.

3. The method of claim 1, wherein the target posture is standing.

4. The method of claim 1, wherein the target posture is lying down.

5. The method of claim 1, wherein displaying for the user the determined activity metric values comprises displaying a trend diagram of activity over time based on the activity metric values determined over time.

6. The method of claim 1, wherein displaying for the user the determined activity metric values comprises displaying a graphical representation of percentages of time that the activity metric values were within each of a plurality of ranges.

7. The method of claim 1, wherein displaying for the user the determined activity metric values in a manner that is indicative of efficacy of the neurostimulation therapy delivered to the patient comprises displaying for the user the determined activity metric values in a manner that is indicative of an amount of time that the patient was upright and active.

8. The method of claim 1,
further comprising associating each of the determined activity levels with a therapy parameter set, selected from among a plurality of therapy parameter sets, according to which the implantable medical device delivered the neurostimulation therapy to the patient when the activity levels were determined,
wherein displaying for the user the determined activity metric values comprises displaying the determined activity metric values in a manner that is indicative of the relative efficacy of the plurality of therapy parameter sets.

9. The method of claim 1, further comprising:
determining an average number of posture transitions over a period of time; and
displaying for the user the determined average number of posture transitions over the period of time in a manner that is indicative of efficacy of the neurostimulation therapy delivered to the patient.

10. The method of claim 1, wherein the neurostimulation therapy comprises at least one of spinal cord stimulation, a movement disorder therapy, a psychological disorder therapy, deep brain stimulation, a tremor therapy, a Parkinson's disease therapy, or an epilepsy therapy.

11. A medical system comprising:
one or more sensors, each of the sensors generating a signal as a function of at least one of activity or posture of a patient;
an implantable medical device that delivers a neurostimulation therapy to a patient; and
a processor that:
determines whether the patient is in a target posture based on at least one of the signals,
periodically determines an activity level of the patient based on at least one of the signals when the patient is in the target posture, and
periodically determines values of at least one activity metric based on the activity levels determined when the patient was in the target posture; and
a computing device that displays for a user the determined activity metric values in a manner that is indicative of efficacy of the neurostimulation therapy delivered to the patient.

12. The medical system of claim 11, wherein the target posture is upright.

13. The medical system of claim 11, wherein the target posture is standing.

14. The medical system of claim 11, wherein the target posture is lying down.

15. The medical system of claim 11, wherein the computing device displays a trend diagram of activity over time based on the activity metric values determined over time.

16. The medical system of claim 11, wherein the computing device displays a graphical representation of percentages of time that the activity metric values were within each of a plurality of ranges.

17. The medical system of claim 11, wherein the computing device displays for the user the determined activity metric values in a manner that is indicative of an amount of time that the patient was upright and active.

18. The medical system of claim 11,
wherein the processor further comprising associates each of the determined activity levels with a therapy parameter set, selected from among a plurality of therapy parameter sets, according to which the implantable medical device delivered the neurostimulation therapy to the patient when the activity levels were determined, and
wherein the computing device displays the determined activity metric values in a manner that is indicative of the relative efficacy of the plurality of therapy parameter sets.

19. The medical system of claim 11,
wherein the processor further determines an average number of posture transitions over a period of time, and
wherein the computing device displays for the user the determined average number of posture transitions over the period of time in a manner that is indicative of efficacy of the neurostimulation therapy delivered to the patient.

20. A medical system comprising:
means for monitoring a plurality of signals, each of the signals generated as a function of at least one of activity or posture of the patient;
means for determining whether the patient is in a target posture based on at least one of the signals;
means for periodically determining an activity level of the patient based on at least one of the signals when the patient is in the target posture;
means for periodically determining values of at least one activity metric based on the activity levels determined when the patient was in the target posture; and
means for presenting the determined activity metric values to a user in a manner that is indicative of efficacy of a neurostimulation therapy delivered to the patient.

21. A non-transitory computer-readable medium comprising instructions that cause a processor to:
monitor a plurality of signals, each of the signals generated by a sensor of the implantable medical device system as a function of at least one of activity or posture of the patient;
determine whether the patient is in a target posture based on at least one of the signals;
periodically determine an activity level of the patient based on at least one of the signals when the patient is in the target posture;
periodically determine values of at least one activity metric based on the activity levels determined when the patient was in the target posture; and
cause display of the determined activity metric values for a user in a manner that is indicative of efficacy of a neurostimulation therapy delivered to the patient.

* * * * *